(12) United States Patent
Harkness et al.

(10) Patent No.: US 11,851,459 B2
(45) Date of Patent: Dec. 26, 2023

(54) METHODS AND USES OF MODULATORS OF ANAPHASE PROMOTING COMPLEX (APC) ACTIVITY FOR TREATING CANCER

(71) Applicant: University of Saskatchewan, Saskatoon (CA)

(72) Inventors: Troy Harkness, Saskatoon (CA); Terra Gayle Arnason, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 309 days.

(21) Appl. No.: 17/044,602

(22) PCT Filed: Apr. 4, 2019

(86) PCT No.: PCT/CA2019/050414
§ 371 (c)(1),
(2) Date: Oct. 1, 2020

(87) PCT Pub. No.: WO2019/191847
PCT Pub. Date: Oct. 10, 2019

(65) Prior Publication Data
US 2021/0101947 A1    Apr. 8, 2021

Related U.S. Application Data

(60) Provisional application No. 62/744,272, filed on Oct. 11, 2018.

(30) Foreign Application Priority Data

Apr. 4, 2018    (WO) ................ PCT/CA2018/050414

(51) Int. Cl.
| C07K 14/47 | (2006.01) |
| A61P 35/00 | (2006.01) |
| A61K 38/00 | (2006.01) |
| A61K 45/06 | (2006.01) |

(52) U.S. Cl.
CPC .......... *C07K 14/4705* (2013.01); *A61P 35/00* (2018.01); *A61K 38/00* (2013.01); *A61K 45/06* (2013.01)

(58) Field of Classification Search
None
See application file for complete search history.

(56) References Cited

U.S. PATENT DOCUMENTS

| 6,184,205 B1 | 2/2001 | Sparks et al. |
| 2015/0197765 A1 | 7/2015 | Guo et al. |
| 2017/0322219 A1 | 10/2017 | Wandall et al. |

OTHER PUBLICATIONS

Kastl et al. "Mad2 Inhibitor-1 (M2I-1): A Small Molecule Protein-Protein Interaction Inhibitor Targeting the Mitotic Spindle Assembly Checkpoint" ACS Chem. Biol. 10:1661-1666. (Year: 2015).*
Goodwin et al. "Effect of Metformin vs Placebo on Invasive Disease-Free Survival in Patients with Breast Cancer The mA.32 Randomized Clinical Trial" J. Amer. Med. Assoc. 327:1963-1973. (Year: 2022).*
Thu et al. "Disruption of the anaphase-promoting complex confers resistance to TTK inhibitors in triple-negative breast cancer" Proc. Natl. Acad. Sci. 115:E1570-E1577. (Year: 2017).*
Camacho et al. "Metformin in breast cancer—an evolving mystery" Breast Cancer Res. 17:88 (Year: 2015).*
Beddard P "A Study of Investigational Drug CFI-402257 in Patients with Advanced Solid Tumors" ClinicalTrials.gov NCT02792465. (Year: 2016).*
NCBI Blast sequence arvrrlt (retrieved from https://blast.ncbi.nlm.nih.gov/Blast.cgi on Feb. 23, 2022, 27 pages) (Year: 2022).
Odaert et al. (Nonnative capping structure initiates helix folding in an annexin I fragment. A H NMR conformational study Biochemistry 34 1995 pp. 12820-12829) (Year: 1995).
Allen et al. (Why are a3 ions rarely observed?' J Am Soc Mass Spectrom 2008 v19 pp. 1764-1770). (Year: 2008).
Panchenko et al. ('Prediction of functional sites by analysis of sequence and structure conservation' Protein Science v13 2004 pp. 884-892) (Year: 2004).
Pommie et al. ('IMGT standardized criteria for statistical analysis of immunoglobulin V-REGION amino acid properties' Journal of Molecular Recognition 2004 v17 pp. 17-32) (Year: 2004).
Kastl et al. Mad2 Inhibitor-1 (M2I-1): A Small Molecule Protein-Protein Interaction Inhibitor Targeting the Mitotic Spindle Assembly Checkpoint. ACS Chemical Biolog. 2015. 10:1661-1666.
NCBI Blast sequence rvrrlt (retrieved from https://blast.ncbi.nlm.nih.gov/Blast.cgi on Aug. 19, 2021, 19 pages) (Year: 2021).
International Preliminary Report on Patentability (IPRP), international application No. PCT/CA2019/050414, dated Jul. 12, 2019.
Davies et al. (2017) Metformin inhibits the development, and promotes the resensitization, of treatment-resistant breast cancer. PLoS ONE , Dec. 6, 2017, vol. 12, pp. 1-22.
International Preliminary Report on Patentbility (IPRP), internatioinal application No. PCT/CA2018/050414, dated Apr. 4, 2017.
Kastl et al., ACS Chemical Biology, 2015, vol. 10, pp. 1661-1666.
Wassmann and Benezra, Proceedings of the National Academy of Science USA, 1998, vol. 95, pp. 11193-11198.
Harkness, T.A.A., Current Genomics, 2006, vol. 7(4), pp. 263-272.
Malo et al., Aging, Apr. 2016 (Apr. 2016), vol. 8(4), pp. 810-828.
Postnikoff et al., PLoS Genetics, Mar. 2012 (Mar. 2012), vol. 8(3), pp. 1-13.
Wasch and Engelbert, Oncogene, 2005, vol. 24, pp. 1-10.

(Continued)

*Primary Examiner* — Sudhakar Katakam
*Assistant Examiner* — Zachary J Miknis
(74) *Attorney, Agent, or Firm* — Bereskin & Parr LLP/S.E.N.C.RL., s.r.l.; Ainslie Parsons

(57) ABSTRACT

Methods and uses of activators of the APC complex for treating cancer in a subject, inhibiting the growth of a cancer cell, increasing sensitivity to a cancer treatment in a cancer cell or a subject and/or reducing resistance to a cancer treatment in a cancer cell or a subject.

13 Claims, 32 Drawing Sheets

Specification includes a Sequence Listing.

(56) References Cited

OTHER PUBLICATIONS

Juganbayar et al., Small Peptides Homologous to the Histone Variant Htz1 Extend Yeast Lifespan in an Anaphase Promoting Complex-Dependent Manner, Epigenetics Meeting—Epigenetics Eh!—London, ON, Canada—Jun. 24-27, 2014.
Davies et al. (2017) Metformin inhibits the development, and promotes the resensitization, of treatment-resistant breast cancer. PLoS One 12(12): e0187191.
Harkness et al. (2004) A functional analysis reveals dependence on the anaphase-promoting complex for prolonged life span in yeast. Genetics 168:759-74.
Postnikoff and Harkness (2014). Replicative and chronological life-span assays. Methods Mol Biol 1163:223-7.
Postnikoff et al (2012). The yeast forkhead transcription factors fkh1 and fkh2 regulate lifespan and stress response together with the anaphase-promoting complex. PLoS Genet 8:e1002583.
Menzel et al. (2014). The anaphase promoting complex regulates yeast lifespan and rDNA stability by targeting Fob1 for degradation. Genetics 196:693-709.
Harkness el al. (2002). The ubiquitin-dependent targeting pathway in Saccharomyces cerevisiae plays a critical role in multiple chromatin assembly regulatory steps. Genetics 162:615-32.
Harkness et al (2005). Contribution of CAF-I to anaphase-promoting-complex-mediated mitotic chromatin assembly in Saccharomyces cerevisiae. Eukaryot Cell 4:673-84.
Turner et al. (2010). The Saccharomyces cerevisiae anaphase-promoting complex interacts with multiple histone-modifying enzymes to regulate cell cycle progression. Eukaryot Cell 9:1418-31.
Islam et al. (2011). Antagonistic Gcn5-Hda1 interactions revealed by mutations to the Anaphase Promoting Complex in yeast. Cell Div 6:13.
Jiao et al (2015). The SNF1 Kinase Ubiquitin-associated Domain Restrains Its Activation, Activity, and the Yeast Life Span. J Biol Chem 290:15393-404.
Malo et al (2016). Mitotic degradation of yeast Fkh1 by the Anaphase Promoting Complex is required for normal longevity, genomic stability and stress resistance. Aging 8:810-30.
Feser et al. (2010). Elevated histone expression promotes life span extension. Mol Cell 39:724-35.
Yu et al. (2013). Histone variant Htz1 promotes histone H3 acetylation to enhance nucleotide excision repair in Htz1 nucleosomes. Nucleic Acids Res 41:9006-19.

Millar et al. (2006). Acetylation of H2AZ Lys 14 is associated with genome-wide gene activity in yeast. Genes Dev 20:711-22.
Harreman et al. (2009). Distinct ubiquitin ligases act sequentially for RNA polymerase II polyubiquitylation. PNAS 106:20705-10.
Ribar et al. (2007). ELA1 and CUL3 are required along with ELC1 for RNA polymerase II polyubiquitylation and degradation in DNA-damaged yeast cells. MCB 27:3211-6.
Hanlon et al. (2011). The stress response factors Yap6, Cin5, Phd1, and Skn7 direct targeting of the conserved co-repressor Tup 1-Ssn6 in S. cerevisiae PLoS One 6:e19060.
Furuchi et al. (2001). Two nuclear proteins, Cin5 and Ydr259c, confer resistance to cisplatin in Saccharomyces cerevisiae. Mol Pharmacol 59(3):470-4.
Jackson et al. (2000). Novel roles for elongin C in yeast. Biochim Biophys Acta 1491:161-76.
Nevitt et al. (2004). YAP4 gene expression is induced in response to several forms of stress in Saccharomyces cerevisiae. Yeast 21:1365-74.
Thornton et al. (2006) An architectural map of the anaphase-promoting complex. Genes Dev 20: 449-460.
Edwards et al. (2018). Perinatal Hypoxic-Ischemic Encephalopathy and Neuroprotective Peptide Therapies: A Case for Cationic Arginine-Rich Peptides (CARPs). Brain Sciences, 8(8), 147.
Henriques et al. (2005). Translocation of beta-galactosidase mediated by cell-penetrating peptide pep-1 into lipid vesicles and human HeLa cells is driven by membrane electrostatic potential. Biochemistry 44:10189-10198.
Mae et al. (2005) Internalisation of cell-penetrating peptides into tobacco protoplasts. Biochim Biophys Acta 1669:101-107.
Meloni et al. (2015) Poly-arginine and arginine-rich peptides are neuroprotective in stroke models. J. Cereb. Blood Flow Metab. 2015;35:993-1004.
Pooga M. et al. (2001) Cellular translocation of proteins by transportan. FASEB J 15:1451-1453.
Rudolph C. et al. (2003) Oligomers of the arginine-rich motif of the HIV-1TAT protein are capable of transferring plasmid DNA into cells. J Biol Chem 278(13):11411-11418.
Copolovic et al. (2014), Cell-Penetrating Peptides: Design, Synthesis, and Applications, ACS Nano, 2014, 8(3), pp. 1972-1994.
Eloy, N.B., et al.,"The Role of the Anaphase-Promoting Complex/Cylcosome in Plant Growth", Crit Rev Plant Sci. 2015; 24-487-505.
NCBI Blast sequence prplppl (retrieved from https://blast.ncbi.nlm.nih.gov/blast.cgi on Dec. 5, 2022, 32 pages) (Year: 2022).

\* cited by examiner

WT – 2 days stationary phase

Fig. 3C

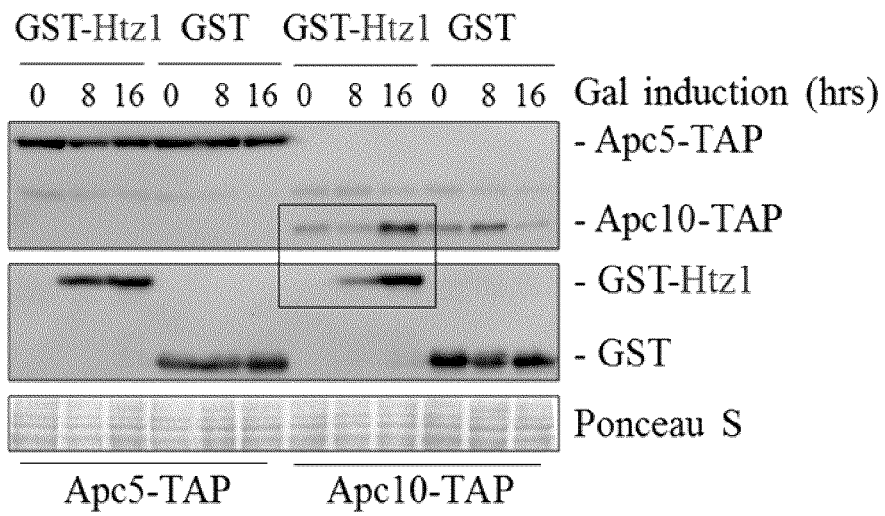

Fig. 4

```
                                 Ability of mutant
            - a/c - - -          to enhance growth
    A      AA  A A  A
    NGSSHNDLRVRRLTLISRLC                              C43-4
71-VLELAGNAAKDLKVKRITPRHLQLAIR-98                     Htz1
   28-REKKQKCLKQVRRLSLISPKKYIMP-43                    Cst9
   391-IHSKSMSVERGIRWELISRLCPNSTGA-417                Rpt1
         144-CDLSVVDLHIRRLTPGAKIG-163                 Svf1
     374-KINGNTLNDLVIKRLLEKDVTLRISIQ-401              Elm1
          13-SFPLQVLR-RRLT-ISSLTSFQPTT-35             Mto1
         79-VGFDAVVDVR-RRLT-ISHLQNLLDS-102            YEL023c
                     ?        ?
                Required for  Required for
                interaction with  activity
                    Apc10
```

```
         RMPQWWQWMWVRAK            C2-4B
 131-YHEKMPKWSQWVAKGSAAYL-150      Shh3
 999-DNVTTQWREWMFPHNET-1015        Sum1
 186-SQCREKSQWKWFLNLCYV-203        Scc4
  16-ENDKEGWQRLWKSYQDFY-33         Hpa2
1231-LMPGFWTFMWKLSPYT-1246         Pdr18
 661-MAGDIWRKWLWRELEESS-678        Oca5
1354-VSLMPGFWTFMWK-AS-1368         Snq2
```

E. coli Thioredoxin

Canine 1 – MDR
Canine 2 – MDR
Canine 3 – drug sensitive
Canine 4 – drug sensitive
Canine 5 - MDR

OSW^DOX

Fig. 20A
Fig. 20B
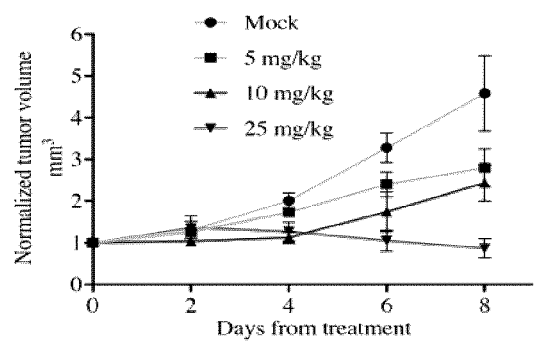
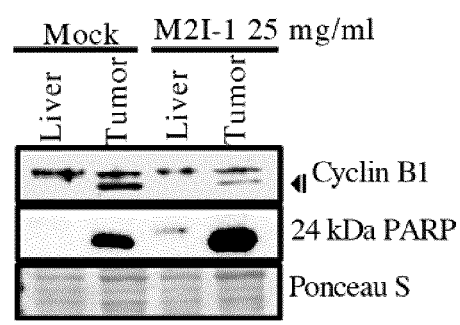
Fig. 21
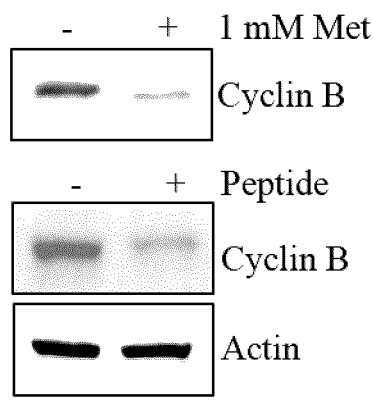

- + Peptide/TAT2
Cyclin B
$PARP^{tot}$
$PARP^{29\ kD\ cleavage}$
TFPI1

Ponceau S

+ 1 uM DOX/24 hrs.

MDA-MB-231 cells

SEQUENCE LISTING

```
<160> NUMBER OF SEQ ID NOS: 48

<210> SEQ ID NO 1
<211> LENGTH: 20
<212> TYPE: PRT
<213> ORGANISM: Artificial Sequence
<220> FEATURE:
<223> OTHER INFORMATION: Synthetic construct

<400> SEQUENCE: 1

Asn Gly Ser Ser His Asn Asp Leu Arg Val Arg Arg Leu Thr Leu Ile
1               5                   10                  15

Ser Arg Leu Cys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic construct

<400> SEQUENCE: 2

Asn Gly Ser Ser His Asn Asp Ala Arg Val Arg Arg Leu Thr Leu Ile
1               5                   10                  15

Ser Arg Leu Cys
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic construct

<400> SEQUENCE: 3

Cys Glu Cys Leu Glu Thr Glu Thr Phe His Pro Ile Thr Arg His Leu
1               5                   10                  15

Ile Val Pro Val
            20

<210> SEQ ID NO 4
<211> LENGTH: 11
<212> TYPE: PRT
<213> ORGANISM: Artificial Sequence
<220> FEATURE:
<223> OTHER INFORMATION: Synthetic construct

<400> SEQUENCE: 4

Arg Met Pro Gln Trp Trp Gln Trp Met Trp Val
1               5                   10

<210> SEQ ID NO 5
<211> LENGTH: 25
<212> TYPE: PRT
```

```
<213> ORGANISM: Artificial Sequence
<220> FEATURE:
<223> OTHER INFORMATION: Synthetic construct

<400> SEQUENCE: 5

Pro Ser Tyr Asn Thr Ile Lys Tyr His Glu Thr His Gly Gly Arg His
1               5                   10                  15

Pro Arg Arg Gln Arg Lys Arg Pro Ile
            20                  25

<210> SEQ ID NO 6
<211> LENGTH: 20
<212> TYPE: PRT
<213> ORGANISM: Artificial Sequence
<220> FEATURE:
<223> OTHER INFORMATION: Synthetic construct

<400> SEQUENCE: 6

Gly Ala Leu Lys Glu Val Cys Ile Cys Ile Val Glu Ser Val Gly Gly
1               5                   10                  15

Glu Val Phe Ser
            20

<210> SEQ ID NO 7
<211> LENGTH: 22
<212> TYPE: PRT
<213> ORGANISM: Artificial Sequence
<220> FEATURE:
<223> OTHER INFORMATION: Synthetic construct

<400> SEQUENCE: 7

Ser Lys Trp Thr Trp Arg Met Cys Met Ser Trp Thr Val Asp Arg Phe
1               5                   10                  15

Ala Pro Val Pro Trp Pro
            20

<210> SEQ ID NO 8
<211> LENGTH: 3
<212> TYPE: PRT
<213> ORGANISM: Artificial Sequence
<220> FEATURE:
<223> OTHER INFORMATION: Synthetic construct

<400> SEQUENCE: 8

Phe Leu Cys
1

<210> SEQ ID NO 9
<211> LENGTH: 20
<212> TYPE: PRT
<213> ORGANISM: Artificial Sequence
<220> FEATURE:
<223> OTHER INFORMATION: Synthetic construct

<400> SEQUENCE: 9

Arg Arg Cys Leu Ser Ile Arg Thr Glu Asn Leu Ala Trp Glu Gly Lys
1               5                   10                  15

Phe Leu Arg Val
            20

<210> SEQ ID NO 10
<211> LENGTH: 20
<212> TYPE: PRT
<213> ORGANISM: Artificial Sequence
<220> FEATURE:
```

```
<223> OTHER INFORMATION: Synthetic construct

<400> SEQUENCE: 10

Val Arg Gln Lys Ser Asp Lys Glu Tyr Glu Arg Val Leu Gly Leu Gly
1               5                   10                  15

Leu Arg Arg Leu
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic construct

<400> SEQUENCE: 11

Ser Trp Leu Asn Gly Ser Gly Gly Val Val Leu Trp Leu Phe Ser Asn
1               5                   10                  15

Phe Cys Cys Gly
            20

<210> SEQ ID NO 12
<211> LENGTH: 13
<212> TYPE: PRT
<213> ORGANISM: Artificial Sequence
<220> FEATURE:
<223> OTHER INFORMATION: Synthetic construct

<400> SEQUENCE: 12

Gly Ser Ser His Asn Asp Leu Arg Val Arg Arg Leu Thr
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Synthetic construct

<400> SEQUENCE: 13

Glu Thr Glu Thr Phe His Pro Ile Thr Arg His Leu Ile Val Pro
1               5                   10                  15

<210> SEQ ID NO 14
<211> LENGTH: 9
<212> TYPE: PRT
<213> ORGANISM: Artificial Sequence
<220> FEATURE:
<223> OTHER INFORMATION: Synthetic construct

<400> SEQUENCE: 14

Arg Met Pro Gln Trp Trp Gln Trp Met
1               5

<210> SEQ ID NO 15
<211> LENGTH: 9
<212> TYPE: PRT
<213> ORGANISM: Artificial Sequence
<220> FEATURE:
<223> OTHER INFORMATION: Synthetic construct

<400> SEQUENCE: 15

Pro Val Asn Gly Glu Arg Trp Ala Pro
1               5
```

```
<210> SEQ ID NO 16
<211> LENGTH: 24
<212> TYPE: PRT
<213> ORGANISM: Artificial Sequence
<220> FEATURE:
<223> OTHER INFORMATION: Synthetic construct

<400> SEQUENCE: 16

Gly Arg Met Leu Met Thr Tyr Leu Met Tyr Phe Met Val Leu Trp Val
1               5                   10                  15

Pro Arg Pro Trp Gly Pro Pro Leu
            20

<210> SEQ ID NO 17
<211> LENGTH: 10
<212> TYPE: PRT
<213> ORGANISM: Artificial Sequence
<220> FEATURE:
<223> OTHER INFORMATION: Synthetic construct

<400> SEQUENCE: 17

Arg Lys Lys Arg Arg Gln Arg Arg Arg Arg
1               5                   10

<210> SEQ ID NO 18
<211> LENGTH: 20
<212> TYPE: PRT
<213> ORGANISM: Artificial Sequence
<220> FEATURE:
<223> OTHER INFORMATION: Synthetic construct

<400> SEQUENCE: 18

Asn Ala Ser Ser His Asn Asp Leu Arg Val Arg Arg Leu Thr Leu Ile
1               5                   10                  15

Ser Arg Leu Cys
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic construct

<400> SEQUENCE: 19

Asn Gly Ser Ser His Asn Ala Leu Arg Val Arg Arg Leu Thr Leu Ile
1               5                   10                  15

Ser Arg Leu Cys
            20

<210> SEQ ID NO 20
<211> LENGTH: 20
<212> TYPE: PRT
<213> ORGANISM: Artificial Sequence
<220> FEATURE:
<223> OTHER INFORMATION: Synthetic construct

<400> SEQUENCE: 20

Asn Gly Ser Ser His Asn Asp Ala Arg Val Arg Arg Leu Thr Leu Ile
1               5                   10                  15

Ser Arg Leu Cys
            20

<210> SEQ ID NO 21
<211> LENGTH: 20
```

```
<212> TYPE: PRT
<213> ORGANISM: Artificial Sequence
<220> FEATURE:
<223> OTHER INFORMATION: Synthetic construct

<400> SEQUENCE: 21

Asn Gly Ser Ser His Asn Asp Leu Arg Ala Arg Arg Leu Thr Leu Ile
1               5                   10                  15

Ser Arg Leu Cys
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic construct

<400> SEQUENCE: 22

Asn Gly Ser Ser His Asn Asp Leu Arg Val Arg Ala Leu Thr Leu Ile
1               5                   10                  15

Ser Arg Leu Cys
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic construct

<400> SEQUENCE: 23

Asn Gly Ser Ser His Asn Asp Leu Arg Val Arg Arg Leu Ala Leu Ile
1               5                   10                  15

Ser Arg Leu Cys
            20

<210> SEQ ID NO 24
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (8)..(10)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 24

Xaa Ser Ser His Xaa Asp Ala Xaa Xaa Xaa Arg Xaa Thr
1               5                   10

<210> SEQ ID NO 25
<211> LENGTH: 13
<212> TYPE: PRT
<213> ORGANISM: Artificial Sequence
```

<220> FEATURE:
<223> OTHER INFORMATION: Synthetic construct

<400> SEQUENCE: 25

Gly Ser Ser His Asn Asp Ala Arg Val Arg Arg Leu Thr
1               5                   10

<210> SEQ ID NO 26
<211> LENGTH: 18
<212> TYPE: PRT
<213> ORGANISM: Artificial Sequence
<220> FEATURE:
<223> OTHER INFORMATION: Synthetic construct

<400> SEQUENCE: 26

Arg Lys Lys Arg Arg Gln Arg Arg Arg Lys Lys Arg Arg Gln Arg
1               5                   10                  15

Arg Arg

<210> SEQ ID NO 27
<211> LENGTH: 21
<212> TYPE: PRT
<213> ORGANISM: Artificial Sequence
<220> FEATURE:
<223> OTHER INFORMATION: Synthetic construct

<400> SEQUENCE: 27

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 28
<211> LENGTH: 9
<212> TYPE: PRT
<213> ORGANISM: Artificial Sequence
<220> FEATURE:
<223> OTHER INFORMATION: Synthetic construct

<400> SEQUENCE: 28

Arg Arg Arg Arg Arg Arg Arg Arg Arg
1               5

<210> SEQ ID NO 29
<211> LENGTH: 11
<212> TYPE: PRT
<213> ORGANISM: Artificial Sequence
<220> FEATURE:
<223> OTHER INFORMATION: Synthetic construct

<400> SEQUENCE: 29

Thr Ala Leu Asp Trp Ser Trp Leu Gln Thr Glu
1               5                   10

<210> SEQ ID NO 30
<211> LENGTH: 27
<212> TYPE: PRT
<213> ORGANISM: Artificial Sequence
<220> FEATURE:
<223> OTHER INFORMATION: Synthetic construct

<400> SEQUENCE: 30

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu 20                  25

<210> SEQ ID NO 31
<211> LENGTH: 18
<212> TYPE: PRT
<213> ORGANISM: Artificial Sequence
<220> FEATURE:
<223> OTHER INFORMATION: Synthetic construct

<400> SEQUENCE: 31

Ile Ala Ala Arg Ile Lys Leu Arg Ser Arg Gln His Ile Lys Leu Arg
1               5                   10                  15

His Leu

<210> SEQ ID NO 32
<211> LENGTH: 27
<212> TYPE: PRT
<213> ORGANISM: Artificial Sequence
<220> FEATURE:
<223> OTHER INFORMATION: Synthetic construct

<400> SEQUENCE: 32

Val Leu Glu Leu Ala Gly Asn Ala Ala Lys Asp Leu Lys Val Lys Arg
1               5                   10                  15

Ile Thr Pro Arg His Leu Gln Leu Ala Ile Arg
            20                  25

<210> SEQ ID NO 33
<211> LENGTH: 25
<212> TYPE: PRT
<213> ORGANISM: Artificial Sequence
<220> FEATURE:
<223> OTHER INFORMATION: Synthetic construct

<400> SEQUENCE: 33

Arg Glu Lys Lys Gln Lys Cys Leu Lys Cys Val Arg Arg Leu Ser Leu
1               5                   10                  15

Ile Ser Pro Lys Lys Tyr Ile Met Pro
            20                  25

<210> SEQ ID NO 34
<211> LENGTH: 27
<212> TYPE: PRT
<213> ORGANISM: Artificial Sequence
<220> FEATURE:
<223> OTHER INFORMATION: Synthetic construct

<400> SEQUENCE: 34

Ile His Ser Lys Ser Met Ser Val Glu Arg Gly Ile Arg Trp Glu Leu
1               5                   10                  15

Ile Ser Arg Leu Cys Pro Asn Ser Thr Gly Ala
            20                  25

<210> SEQ ID NO 35
<211> LENGTH: 20
<212> TYPE: PRT
<213> ORGANISM: Artificial Sequence
<220> FEATURE:
<223> OTHER INFORMATION: Synthetic construct

<400> SEQUENCE: 35

Cys Asp Leu Ser Val Val Asp Leu His Ile Arg Arg Leu Thr Pro Gly
1               5                   10                  15

Ala Lys Ile Gly

20

<210> SEQ ID NO 36
<211> LENGTH: 27
<212> TYPE: PRT
<213> ORGANISM: Artificial Sequence
<220> FEATURE:
<223> OTHER INFORMATION: Synthetic construct

<400> SEQUENCE: 36

Lys Ile Asn Gly Asn Thr Leu Asn Asp Leu Val Ile Lys Arg Leu Leu
1               5                   10                  15

Glu Lys Asp Val Thr Leu Arg Ile Ser Ile Gln
            20                  25

<210> SEQ ID NO 37
<211> LENGTH: 23
<212> TYPE: PRT
<213> ORGANISM: Artificial Sequence
<220> FEATURE:
<223> OTHER INFORMATION: Synthetic contruct

<400> SEQUENCE: 37

Ser Phe Pro Leu Gly Val Leu Arg Arg Arg Leu Thr Ile Ser Ser Leu
1               5                   10                  15

Thr Ser Phe Gln Pro Thr Thr
            20

<210> SEQ ID NO 38
<211> LENGTH: 24
<212> TYPE: PRT
<213> ORGANISM: Artificial Sequence
<220> FEATURE:
<223> OTHER INFORMATION: Synthetic construct

<400> SEQUENCE: 38

Val Gly Phe Asp Ala Val Val Asp Val Arg Arg Arg Leu Thr Ile Ser
1               5                   10                  15

His Leu Gln Asn Leu Leu Asp Ser
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic construct

<400> SEQUENCE: 39

Tyr His Glu Lys Met Pro Lys Trp Ser Gln Trp Val Ala Lys Gly Ser
1               5                   10                  15

Ala Ala Tyr Leu
            20

<210> SEQ ID NO 40
<211> LENGTH: 17
<212> TYPE: PRT
<213> ORGANISM: Artificial Sequence
<220> FEATURE:
<223> OTHER INFORMATION: Synthetic construct

<400> SEQUENCE: 40

Asp Asn Val Thr Thr Gln Trp Arg Glu Trp Met Phe Pro His Asn Glu
1               5                   10                  15

Thr

<210> SEQ ID NO 41
<211> LENGTH: 18
<212> TYPE: PRT
<213> ORGANISM: Artificial Sequence
<220> FEATURE:
<223> OTHER INFORMATION: Synthetic construct

<400> SEQUENCE: 41

Ser Gln Cys Arg Glu Lys Ser Gln Trp Lys Trp Phe Leu Asn Leu Cys
1               5                   10                  15
Tyr Val

<210> SEQ ID NO 42
<211> LENGTH: 18
<212> TYPE: PRT
<213> ORGANISM: Artificial Sequence
<220> FEATURE:
<223> OTHER INFORMATION: Synthetic construct

<400> SEQUENCE: 42

Glu Asn Asp Lys Glu Gly Trp Gln Arg Leu Trp Lys Ser Tyr Gln Asp
1               5                   10                  15
Phe Tyr

<210> SEQ ID NO 43
<211> LENGTH: 16
<212> TYPE: PRT
<213> ORGANISM: Artificial Sequence
<220> FEATURE:
<223> OTHER INFORMATION: Synthetic construct

<400> SEQUENCE: 43

Leu Met Pro Gly Phe Trp Thr Phe Met Trp Lys Leu Ser Pro Tyr Thr
1               5                   10                  15

<210> SEQ ID NO 44
<211> LENGTH: 18
<212> TYPE: PRT
<213> ORGANISM: Artificial Sequence
<220> FEATURE:
<223> OTHER INFORMATION: Synthetic contruct

<400> SEQUENCE: 44

Met Ala Gly Asp Ile Trp Arg Lys Trp Leu Trp Arg Glu Leu Glu Glu
1               5                   10                  15
Ser Ser

<210> SEQ ID NO 45
<211> LENGTH: 15
<212> TYPE: PRT
<213> ORGANISM: Artificial Sequence
<220> FEATURE:
<223> OTHER INFORMATION: Synthetic construct

<400> SEQUENCE: 45

Val Ser Leu Met Pro Gly Phe Trp Thr Phe Met Trp Lys Ala Ser
1               5                   10                  15

<210> SEQ ID NO 46
<211> LENGTH: 4
<212> TYPE: PRT
<213> ORGANISM: Artificial Sequence
<220> FEATURE:

```
<223> OTHER INFORMATION: Synthetic construct

<400> SEQUENCE: 46

Ser Lys Trp Thr
1

<210> SEQ ID NO 47
<211> LENGTH: 4
<212> TYPE: PRT
<213> ORGANISM: Artificial Sequence
<220> FEATURE:
<223> OTHER INFORMATION: Synthetic construct

<400> SEQUENCE: 47

Met Cys Met Ser
1

<210> SEQ ID NO 48
<211> LENGTH: 10
<212> TYPE: PRT
<213> ORGANISM: Artificial Sequence
<220> FEATURE:
<223> OTHER INFORMATION: Synthetic construct

<400> SEQUENCE: 48

Ser Lys Trp Thr Trp Arg Met Cys Met Ser
1               5                   10
```

METHODS AND USES OF MODULATORS OF ANAPHASE PROMOTING COMPLEX (APC) ACTIVITY FOR TREATING CANCER

CROSS-REFERENCE TO RELATED APPLICATIONS

This application is a national phase entry of PCT/CA2019/050414 filed Apr. 4, 2019 which claims the benefit of priority to PCT Patent Application No. PCT/CA2018/050414 filed Apr. 4, 2018, and U.S. Provisional Application No. 62/744,272 (now expired) filed Oct. 11, 2018, the contents of both of which are incorporated herein by reference in their entirety.

Incorporation of Sequence Listing

A computer readable form of the Sequence Listing "13764-P52925US03_SequenceListing.txt" (13,610 bytes), submitted via EFS-WEB and created on Sep. 21, 2020, is herein incorporated by reference.

FIELD

This disclosure relates to activators of the Anaphase Promoting Complex (APC) and to methods and uses of the APC activators for treating cancer.

BACKGROUND

Evidence is accumulating that cellular lifespan correlates to the damage repair capacity of the cell. Genetic screens in model organisms, from yeast to flies, have demonstrated that genes involved in stress response networks play a decisive role in lifespan determination. Using the brewing yeast model system, it has been shown that regulated cell cycle progression is tightly linked with stress response and normal longevity. Work characterizing the Anaphase Promoting Complex (APC) in yeast, a large highly conserved complex of proteins required for the targeting of substrates for ubiquitin-dependent degradation, has described a number of novel roles and substrates for the APC. The APC is largely known to target proteins that inhibit mitotic progression and G1 maintenance for degradation.

In yeast, the APC has been identified as playing a role in stress response, chromatin assembly regulatory steps, cell cycle progression and longevity (Harkness et al, 2004; Postnikoff et al, 2012; Harkness et al, 2002; Turner et al, 2010).

SUMMARY

Provided herein are methods and uses of Anaphase Promoting Complex (APC) activators for treating cancer in a subject, for inhibiting growth of a cancer cell, for increasing sensitivity to a cancer treatment in a subject or a cancer cell and/or for reducing resistance to a cancer treatment in a subject or a cancer cell.

In one embodiment, the APC activator is or includes one or more compounds each compound comprising a peptide, the peptide comprising:
(a) amino acid sequence GSSHNDLRVRRLT (SEQ ID NO: 12) or an amino acid sequence having at least 50, 60, 70, 80, 90, 95 or 98% sequence identity thereto;
(b) amino acid sequence XSSHXDAXXXRXT (SEQ ID NO: 24), wherein X is any amino acid, optionally wherein the amino acid sequence is GSSHN-DARVRRLT (SEQ ID NO: 25) or an amino acid sequence having at least 50, 60, 70, 80, 90, 95 or 98% sequence identity thereto;
(c) amino acid sequence ETETFHPITRHLIVP (SEQ ID NO: 13) or an amino acid sequence having at least 50, 60, 70, 80, 90, 95 or 98% sequence identity thereto;
(d) amino acid sequence PSYNTIKYHETHGGRH-PRRQRKRPI (SEQ ID NO: 5) or an amino acid sequence having at least 50, 60, 70, 80, 90, 95 or 98% sequence identity thereto;
(e) amino acid sequence GALKEVCICIVESVGGEVFS (SEQ ID NO: 6) or an amino acid sequence having at least 50, 60, 70, 80, 90, 95 or 98% sequence identity thereto;
(f) an amino acid sequence that comprises SKWT (SEQ ID NO: 46) and MCMS (SEQ ID NO: 47), optionally wherein the amino acid sequence comprises SKWTWRMCMS (SEQ ID NO: 48) or an amino acid sequence having at least 50, 60, 70, 80, 90, 95 or 98% sequence identity thereto;
(g) amino acid sequence RRCLSIRTENLAWEGKFLRV (SEQ ID NO: 9) or an amino acid sequence having at least 50, 60, 70, 80, 90 or 98% sequence identity thereto;
(h) amino acid sequence VRQKSDKEY-ERVLGLGLRRL (SEQ ID NO: 10) or SWLNGSGGWLWLFSNFCCG (SEQ ID NO: 11) or an amino acid sequence having at least 50, 60, 70, 80, 90 or 98% sequence identity with VRQKSDKEY-ERVLGLGLRRL (SEQ ID NO: 10) or SWLNGSGGWLWLFSNFCCG (SEQ ID NO: 11);
(i) amino acid sequence RMPQWWQWMWV (SEQ ID NO: 4) or an amino acid sequence having at least 50, 60, 70, 80, 90, 95 or 98% sequence identity with or RMPQWWQWMWV (SEQ ID NO: 4);
(j) amino acid sequence PVNGERWAP (SEQ ID NO: 15) or an amino acid sequence having at least 50, 60, 70, 80, 90, 95 or 98% sequence identity with PVNGER-WAP (SEQ ID NO: 15);
or a conservatively substituted variant of any one of (a) to (j) or a part of any one of (a) to (j) comprising at least 5, 6, 7 or 8 contiguous amino acids of any thereof;
and optionally wherein the peptide has a maximum length of 30 amino acids.

Suitable peptides include peptides that increase the viability of an APC5 temperature sensitive mutant yeast cell and/or an APC10 mutant yeast cell and/or binds the APC.

In one embodiment, the peptide comprises or consists of amino acid sequence GSSHNDLRVRRLT (SEQ ID NO: 12) or NGSSHNDLRVRRLTLISRLC (SEQ ID NO: 1) or a conservatively substituted variant thereof.

In another embodiment, the peptide comprises or consists of amino acid sequence PSYNTIKYHETHGGRH-PRRQPKRPI (SEQ ID NO: 5) or a conservatively substituted variant thereof.

In another embodiment, the peptide comprises or consists of amino acid sequence GALKEVCICIVESVGGEVFS (SEQ ID NO: 6) or a conservatively substituted variant thereof.

In another embodiment, the peptide comprises or consists of an amino acid sequence NGSSHNDLRVRRLTLISRLC (SEQ ID NO: 1), NGSSHNDARVRRLTLISRLC (SEQ ID NO: 2), CECLETETFHPITRHLIVPV (SEQ ID NO: 3), RMPQWWQWMWV (SEQ ID NO: 4), PSYNTIKYHETH-GGRHPRRQPKRPI (SEQ ID NO: 5), GALKEVCI-CIVESVGGEVFS (SEQ ID NO: 6), SKWTWRMCMSWTVDRFAPVPWP (SEQ ID NO: 7), RRCLSIRTENLAWEGKFLRV (SEQ ID NO: 9), PVNGERWAP (SEQ ID NO: 15) or a conservatively substituted variant thereof.

In one embodiment, the peptide increases the viability of an APC5 temperature sensitive mutant yeast cell.

In another embodiment, the peptide comprises or consists of amino acid sequence VRQKSDKEYERVLGLGLRRL (SEQ ID NO: 10) or SWLNGSGGWLWLFSNFCCG (SEQ ID NO: 11) or a conservatively substituted variant thereof.

In another embodiment, the peptide is conjugated to a cell-penetrating peptide, optionally TAT2, TAT, Pep1, R9, TAT-NBD, Transportan, pVEC, penetratin, VP22, a polyarginine-based peptide or a calcitonin-derived peptide.

In another embodiment, the APC activator comprises or is a molecule that binds and inhibits activity of Mad2, optionally Mad2 inhibitor-1.

In another embodiment, the APC activator comprises or is TTKi or metformin.

In another embodiment, the subject is a mammal, optionally a human.

In another embodiment, the cancer to be treated is a cancer characterized by defective APC function and/or levels.

In another embodiment, the cancer is breast cancer, optionally triple negative breast cancer.

In another embodiment, the cancer is lymphocytic cancer or leukemia.

In another embodiment, the method further comprises administering a chemotherapeutic to the subject.

In another embodiment, the chemotherapeutic is administered prior to, overlapping with, concurrently with, and/or after administration of the APC activator.

The disclosure also provides a composition comprising an APC activator and a carrier, wherein the composition is for treating cancer in a subject, inhibiting the growth of a cancer cell and/or reducing resistance to a chemotherapeutic in a subject.

The disclosure also provides composition comprising (a) an APC activator and (b) a chemotherapeutic, optionally wherein the chemotherapeutic is a chemotherapeutic used to treat breast cancer, lymphoma or leukemia.

In one embodiment, the chemotherapeutic is doxorubicin, rapamycin, capecitabine, carboplatin, cyclophosphamide, gemcitabine, paclitaxel, vinorelbine and tamoxifen.

In another embodiment, the APC activator is or includes one or more compounds each compound comprising a peptide, the peptide comprising:
  (a) amino acid sequence GSSHNDLRVRRLT (SEQ ID NO: 12) or an amino acid sequence having at least 50, 60, 70, 80, 90, 95 or 98% sequence identity thereto;
  (b) amino acid sequence XSSHXDAXXXRXT (SEQ ID NO: 24), wherein X is any amino acid, optionally wherein the amino acid sequence is GSSHNDARVRRLT (SEQ ID NO: 25) or an amino acid sequence having at least 50, 60, 70, 80, 90, 95 or 98% sequence identity thereto;
  (c) amino acid sequence ETETFHPITRHLIVP (SEQ ID NO: 13) or an amino acid sequence having at least 50, 60, 70, 80, 90, 95 or 98% sequence identity thereto;
  (d) amino acid sequence PSYNTIKYHETHGGRHPRRQRKRPI (SEQ ID NO: 5) or an amino acid sequence having at least 50, 60, 70, 80, 90, 95 or 98% sequence identity thereto;
  (e) amino acid sequence GALKEVCICIVESVGGEVFS (SEQ ID NO: 6) or an amino acid sequence having at least 50, 60, 70, 80, 90, 95 or 98% sequence identity thereto;
  (f) an amino acid sequence that comprises SKWT (SEQ ID NO: 46) and MCMS (SEQ ID NO: 47), optionally wherein the amino acid sequence comprises SKWTWRMCMS (SEQ ID NO: 48) or an amino acid sequence having at least 50, 60, 70, 80, 90, 95 or 98% sequence identity thereto;
  (g) amino acid sequence RRCLSIRTENLAWEGKFLRV (SEQ ID NO: 9) or an amino acid sequence having at least 50, 60, 70, 80, 90 or 98% sequence identity thereto;
  (h) amino acid sequence VRQKSDKEYERVLGLGLRRL (SEQ ID NO: 10) or SWLNGSGGWLWLFSNFCCG (SEQ ID NO: 11) or an amino acid sequence having at least 50, 60, 70, 80, 90 or 98% sequence identity with VRQKSDKEYERVLGLGLRRL (SEQ ID NO: 10) or SWLNGSGGWLWLFSNFCCG (SEQ ID NO: 11);
  (i) amino acid sequence RMPQWWQWMWV (SEQ ID NO: 4) or an amino acid sequence having at least 50, 60, 70, 80, 90, 95 or 98% sequence identity with or RMPQWWQWMWV (SEQ ID NO: 4);
  (j) amino acid sequence PVNGERWAP (SEQ ID NO: 15) or an amino acid sequence having at least 50, 60, 70, 80, 90, 95 or 98% sequence identity with PVNGERWAP (SEQ ID NO: 15);
  or
a conservatively substituted variant of any one of (a) to (j) or a part of any one of (a) to (j) comprising at least 5, 6, 7 or 8 contiguous amino acids of any thereof;
and optionally wherein the peptide has a maximum length of 30 amino acids In another embodiment, the peptide is conjugated to a cell-penetrating peptide, optionally TAT2, TAT, Pep1, R9, TAT-NBD, Transportan, pVEC, penetratin, VP22, a polyarginine-based peptide or a calcitonin-derived peptide.

In an embodiment, the APC activator is or comprises a molecule that binds and inhibits activity of Mad2. Optionally, the APC activator is or comprises Mad2 inhibitor-1. In another embodiment, the APC activator is or comprises TTKi. In a further embodiment, the APC activator is or comprises metformin. In an embodiment, the APC activator is comprised in a composition, optionally comprising a pharmaceutically suitable carrier.

The disclosure also provides use of the APC activator or composition as described above for treating cancer, in a subject, inhibiting the growth of a cancer cell, increasing sensitivity to a cancer treatment in a subject or a cancer cell and/or reducing resistance to a chemotherapeutic in a subject or cancer cell.

In one embodiment, the cancer is breast cancer, lymphoma or leukemia.

The disclosure also provides a peptide comprising (a) amino acid sequence PVNGERWAP (SEQ ID NO: 15) or (b) an amino acid sequence having at least 50, 60, 70, 80, 90, 95 or 98% sequence identity thereto or
a conservatively substituted variant of (a) or (b) or a part of (a) or (b) comprising at least 5, 6, 7 or 8 contiguous amino acids of any thereof; and optionally wherein the peptide has a maximum length of 30 amino acids.

Other features and advantages of the present disclosure will become apparent from the following detailed description. It should be understood, however, that the detailed description and the specific examples while indicating embodiments of the disclosure are given by way of illustration only, since various changes and modifications within the spirit and scope of the disclosure will become apparent to those skilled in the art from this detailed description.

DRAWINGS

Embodiments are described below in relation to the drawings in which:

FIG. 1 shows peptides specific for Apc10 suppress APC mutant temperature sensitive (ts) growth. A. Yeast 2-hybrid (Y2H) cells expressing the APC subunit bait and the galactose inducible Apc10 peptide prey grown on glucose or galactose. Cells co-expressing the Apc5 or Apc10-bait and Apc10 aptamer-prey vectors were spotted onto the appropriate media, in the presence or absence of galactose (the aptamers are Gal inducible), to confirm Y2H interactions. Growth on trp⁻ his⁻ media ensures both plasmids are maintained. A Y2H interaction will drive expression of the ADE2 gene, allowing growth on ade⁻ media. B. Aptamers that bind Apc10 can suppress APC mutant phenotypes. Spot dilutions of apc10Δ cells expressing an empty vector control or the one of 6 Apc10 aptamers tested. Log phase cells were 10-fold serially diluted and spotted onto plates containing either 2% glucose or 2% galactose. The plates were then incubated at 30° C. (permissive temperature) and 34° C. (restrictive stress). C. Peptides identified as binding to the yeast Apc10 APC subunit using the Y2H screen increase growth of wildtype (WT) cells. A series of APC binding peptides were transformed into WT yeast cells, spot diluted, and grown at 30° C. on media supplemented with the normal carbon source (2% glucose). Alternatively, cells were grown on media supplemented with 2% galactose to activate the peptides (the peptides are under the control of a galactose inducible promoter). Galactose also induces a carbon stress, which the cells grow slower on.

FIG. 2 shows the Apc10 binding peptide C43-4 increases replicative lifespan (RLS) in apc5$^{CA}$ cells, and both C43-4 and C2-4B increase stress resistance. A. apc5$^{CA}$ (temperature sensitive allele) cells were transformed with C43-4 or an empty vector. Cells grown overnight in 2% Glu were struck onto 2% Glucose plates and used for the yeast RLS assay. From the top left hand corner of the figures, top line is WT +empty vector, middle line is apc5$^{CA}$+C43-4 peptide and bottom line is apc5$^{CA}$+empty vector. B. WT cells transformed with C43-4, C2-4B or an empty vector were grown to stationary phase in 2% Glu media, then after 2 days spot diluted onto 2% Glu or 2% Gal to induce expression of the peptides.

FIG. 3 shows Htz1, which shares homology with the C43-4 peptide sequence, increases stress resistance, is weakly expressed under normal stress free conditions, partially stabilized in APC mutants, and increases the protein levels of Apc10 when overexpressed. A. Cells expressing HTZ1 were grown under stress conditions. HTZ1 expression, even at low levels, suppressed apc5$^{CA}$ and apc10Δ defects. The cells shown were transformed with either an empty vector or GAL inducible HTZ1. On 2% glucose, the construct is weakly expressed, and this is enough to increase growth of APC mutants at 30° C. HTZ1 at low levels can also suppress oxidative stress defects on $H_2O_2$, and when overexpressed, restore growth on 2% galactose. B. Htz1 accumulates and is unstable in APC mutants during mitosis. The cells shown expressing GST-Htz1 were induced with 0.5% galactose for 16 hours. Nocodazole was added for 3 hours to arrest the cells in mitosis. Cycloheximide (CHX) was then added to inhibit protein synthesis with cells removed at the times shown to assess protein stability. C. Increased expression of Htz1 specifically increases Apc10 protein levels. Apc5-TAP or Apc10-TAP cells expressing Gal inducible GST-Htz1, or the GST empty vector, were grown to mid log phase. 0.5% galactose was added for the time shown followed by GST and TAP westerns. The boxed area highlights induction of Apc10-TAP in response to increasing Htz1 levels. Apc5-TAP is unaffected by Htz1 expression.

FIG. 4 shows a BLAST search for C43-4 aptamer homology. The C43-4 aptamer harbors a region homologous to the *Saccharomyces cerevisiae* H2A.Z protein, a histone H2A variant encoded by HTZ1, as well as other yeast proteins. Incorporation of H2A.Z into nucleosomes prevents spreading of silent chromatin. The homologous HTZ1 region is conserved from yeast to humans. Identical residues are bolded. Similar residues are bolded and underlined. SEQ ID Nos from top to bottom are SEQ ID No: 1, 32, 33, 34, 35, 36, 37, and 38.

FIG. 5 shows a BLAST search for C2-4B aptamer homology. The C2-4B aptamer shares homology with several S. cerevisiae proteins. Ssh3 is a mitochondrial protein while Sum1, Scc4 and Hpa2 interact with chromatin. Sum1 is an interesting candidate to interact with nuclear APC. Sum1 represses the mitotic expression of meiotic genes and is involved in telomere maintenance and chromatin silencing. Identical residues are bolded. Similar residues are bolded and underlined. SEQ ID Nos from top to bottom are SEQ ID No: 4, 39, 40, 41, 42, 43, 44, and 45.

FIG. 6 shows that Htz1 and Sum1 are part of an interaction network. STRING network analyses indicate that Htz1 and Sum1 interact within a pathway involving the HDAC Sir2, and the chromatin assembly factor Asf1. Htz1 and Sum1 also interact within a stress response network involving Fkh1 and Fkh2, and the yeast AMP Kinase Snf1, that all work with the APC to respond to stress and increase lifespan.

FIG. 7 shows Cin5, a protein that binds the apc5$^{CA}$ suppressing peptide Y65, is unstable and controlled in an opposite manner by the ubiquitin ligases (E3's) SCF and APC. A. Cin5-TAP is stabilized in SCF and Elc3 E3 mutants. B. Cin5-TAP is further destabilized in cdc20-1 and apc10Δ mutants. CHX stops all protein synthesis. NaCl induces Cin5 protein expression.

FIG. 8 shows the structure of the conserved Anaphase Promoting Complex (APC). The APC is composed of the TPR arm (the regulatory arm), the structural arm, and the catalytic arm (Eme et al. JMC Evolutionary Biology 2011, 11: 265). The co-activators Cdc20 and Cdh1 interact with Apc3 and Apc7.

FIG. 9 shows construction of random peptide aptamers for use against yeast proteins. Aptamers are small antibody-like peptide sequences expressed from the Thioredoxin (Trx) scaffold. Random DNA sequences are cloned into Trx to be expressed from the Trx scaffold as the variable loop. This stabilizes the aptamer and presents it to target proteins. Aptamers with specific binding capabilities are selected from large random DNA sequence pools.

FIG. 10 shows various C43-4 mutant peptides expressed in WT cells and grown on glucose media at the temperatures shown. The cells were exposed to 5 sec of UV from a UV box prior to incubation. The plus signs define growth compared to the empty vector control.

FIG. 11 shows various C43-4 mutant peptides expressed in WT cells and grown on galactose media to induce the peptides at the temperatures shown. The cells were exposed to 5 sec of UV from a UV box prior to incubation. The plus signs define growth compared to the empty vector control.

Figure 16:
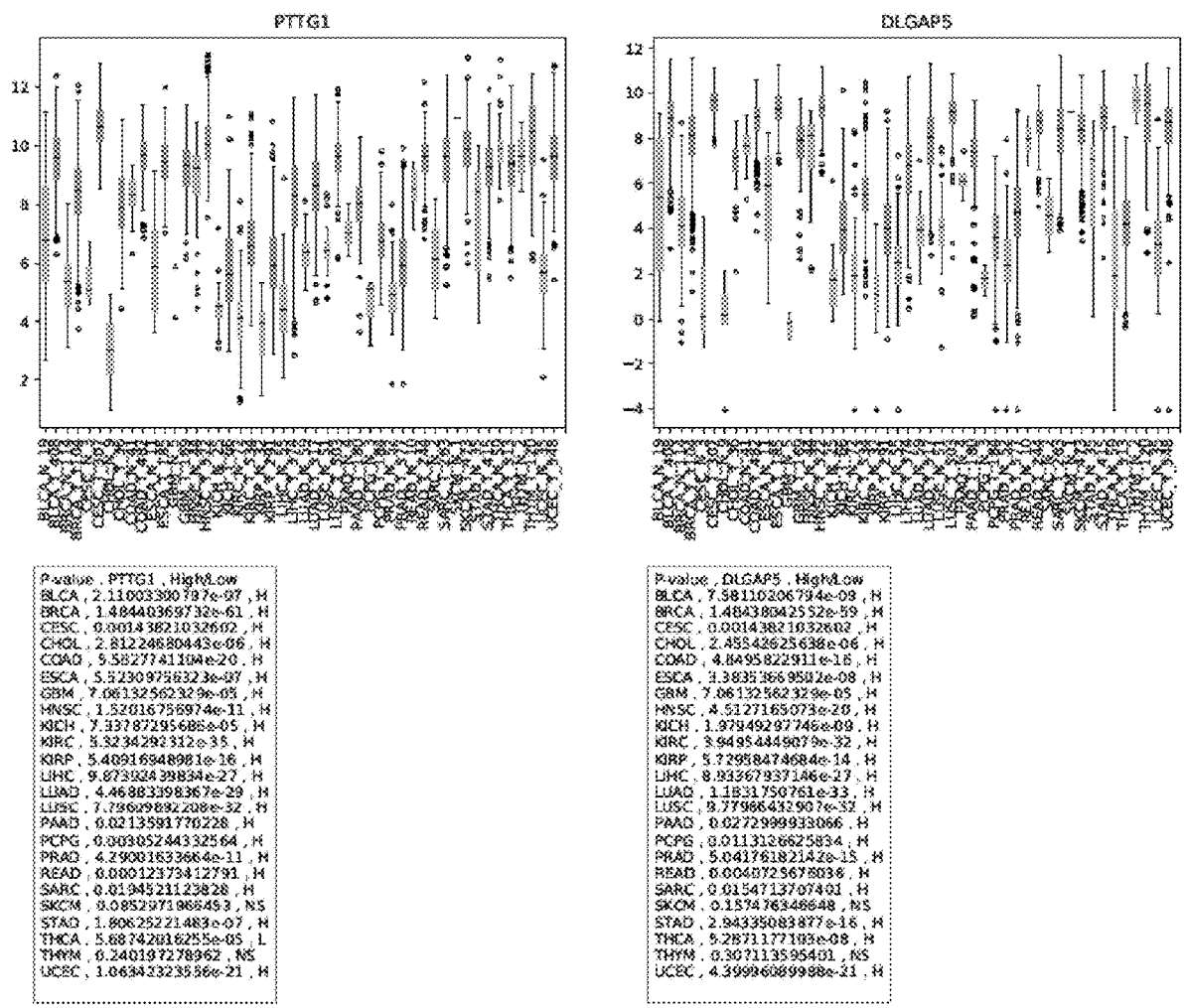
Figure 17A:
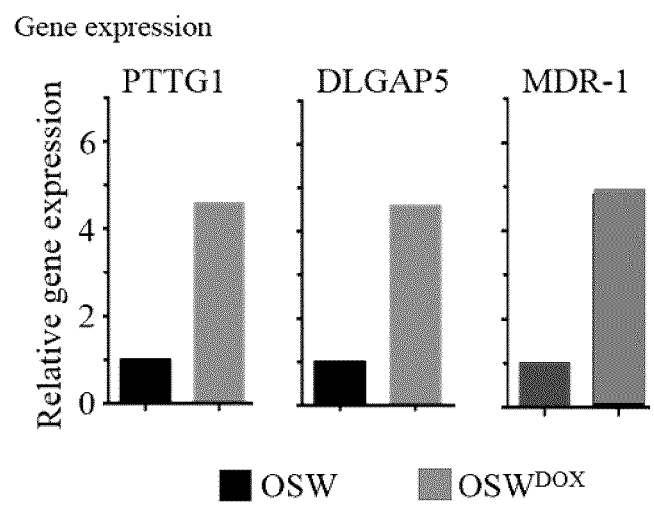
Figure 17B:
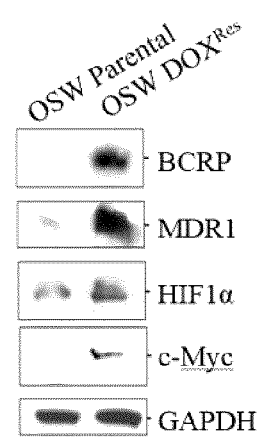
Figure 17C:
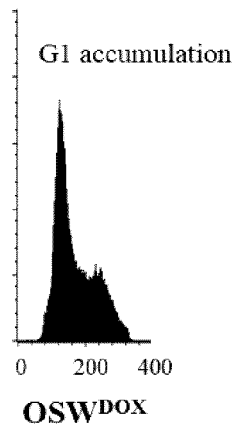
Figure 17D:
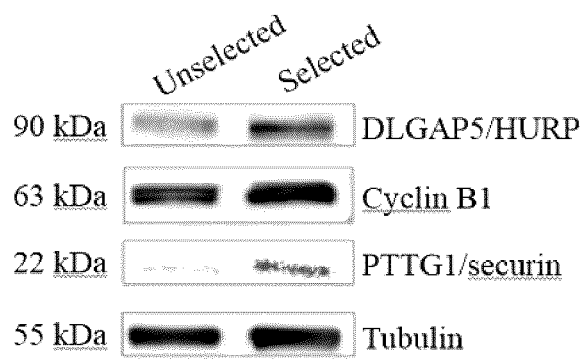
Figure 17E:
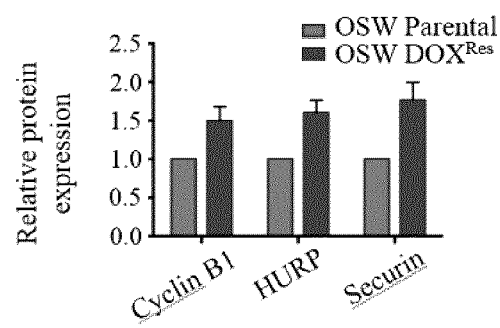

FIG. 16 shows the APC substrate mRNAs PTTG1 and DLGAPS are overexpressed in multiple cancer types. Expression scores for (A) PTTG1 and (B) DLGAPS within 24 different types of cancer and normal tissue from The Cancer Genome Atlas (TCGA). The numbers in x-axis labels denote the number of patient samples in each cancer type. Statistical significance of the difference in expression between the normal and tumor samples is depicted for each cancer type. N.S. not significant. The abbreviation of each cancer in the axis label is represented as described in the TCGA portal.

FIG. 17 shows that APC mitotic protein substrates are elevated in a canine lymphoma cell line selected for Doxorubicin resistance. A. qPCR was performed to measure expression of the APC substrate RNAs PPTG1 and DLGAPS. The multiple drug resistant marker MDR-1 was also measured to show that these were drug resistant cells. B. Westerns were performed to show that the multiple drug resistance protein markers BCRP, MDR-1, HIF1α and c-Myc were elevated in the selected OSW Dox selected cells. C. Cytometry was used to measure the cell cycle stage of Dox selected OSW cells. D. Westerns were performed to show that the APC substrate protein levels of DLGAP5, Cyclin B1 and PTTG1 were all elevated in selected cells. E. The protein bands from three independent westerns shown in D were scanned, normalized to tubulin and plotted.

Figure 18A:
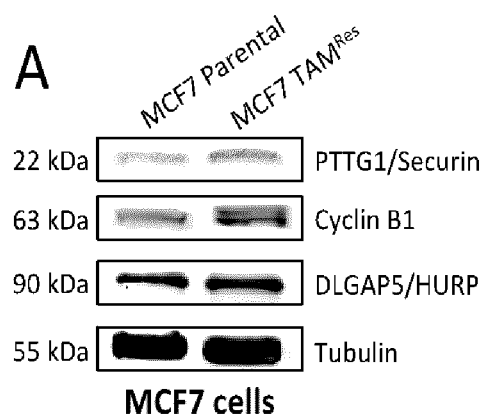
Figure 18B:
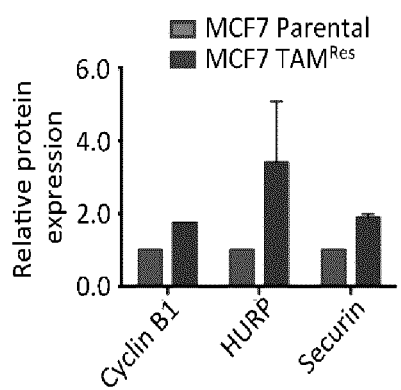

FIG. 18 shows that APC mitotic substrates are elevated in human MCF7 breast cancer cells selected for Tamoxifen resistance. Human MCF7 breast cancer cells were selected for resistance to Tamoxifen. A. Cell lysates were prepared from parental and Tamoxifen resistant cells and used to measure APC substrate protein levels. B. Bands from 3 westerns performed as in were scanned, normalized to Tubulin and plotted.

FIG. 19 shows activation of the APC resensitizes drug resistant cancer cells to chemotherapy. A. M2I-1 (Mad2-inhibitor 1 activates the APC) exposure (18 hrs) is not toxic, yet combination with Doxorubicin (DOX) enhances toxicity. Parental MCF7 human breast cancer cells, or cells selected for resistance to Tamoxifen, were treated with 1 or 5 uM M2I-1. Tamoxifen resistant cells were also treated with both DOX and M2I-1. Cell viability was measured using Trypan Blue staining (3 rpts). B. Protein lysates were prepared from the cells used in A. The APC target HURP was measured using antibodies against HURP. C. Trypan Blue was used to measure viability of parental and DOX resistant OSW canine lymphoma cells pretreated with 1 or 5 μM M2I-1 (18 hrs), followed by 1 μM DOX (48 hrs). Parental cells were only treated with monotherapy (3 rpts). ND, no data. D. OSW matched cells treated with the APC activator M2I-1 were prepared for APC substrate westerns E. Quantification of western protein abundance (3 rpts).

FIG. 20 shows M2I-1 stalls the growth of tumor cells in a mouse model of aggressive triple negative breast cancer (TNBC). A. In vivo study of M2I-1 impact on a human patient derived xenografted breast tumor (4-28 PDX). An increased dose of M2I-1 was given to mice harboring implanted 4-28 tumor fragments (mg/kg i.p. injection (treatment) versus mock (DMSO) day 1, with tumor size measured every other day. B. Western analysis of apoptosis (PARP cleavage—24 kDa band) and APC substrate abundance (Cyclin B) in liver and tumor of treated and control after sacrifice on Day 8.

FIG. 21 shows the APC activating peptide C43-4 expressed from a plasmid in human MCF7 breast cancer cells reduces protein levels of the APC substrate Cyclin B in a manner similar to Metformin; Metformin and the peptide both activate the APC. MCF7 breast cancer cells were treated with 1 mM metformin or transiently transfected with an APC activating peptide (C43-4) for 48 hrs, then harvested for assessment of Cyclin B protein levels. Cyclin B is an APC target.

FIG. 22 shows that transient in vitro expression of the C43-4 peptide enhances DOX sensitivity and increases E3 substrate degradation in MDA-MB-231 TNBC cells. A. Transient transfection of the C43-4 peptide plasmid into human triple negative MDA-MB-231 breast cancer cells followed by Western blot analysis of lysates against Cyclin B, Securin and Cdc20 showing enhanced protein loss. B. Cells in A were treated with DOX (1 uM) for 48 hrs with cell viability measured using an MTT assay kit. The experiment was done in triplicate with standard error of the means shown.

FIG. 23 shows that stable expression of the C43-4 peptide enhances DOX sensitivity and increases E3 substrate degradation in MDA-MB-231 cells. A. Stable integration of C43-4 in MDA-MB-231 cells was established by selection of transfected cells on Geneticin for 7 days. Westerns against APC substrates show APC activation. B. Cells in A were treated with DOX (1 uM) for 48 hrs with cell viability measured using an MTT assay kit. Mean and SEM of 3 biological repeats.

FIG. 24 shows that metastatic potential of MDA-MB-231 cells is blocked by metformin, the APC activator chemical compounds M2I-1 and TTKi, and APC activating peptides. A. An equal number of MDA-MB-231 TNBC cells were grown to confluence in 6 well plates. The cells were then treated with increasing doses of metformin (0, 1, 5 and 10 mM) and a scratch was made in the cell lawn creating a void. At the times shown the number of cell that migrated into the void were counted. The experiment was repeated twice. B. WT MDA-MB-231 cells and cells stably expressing the C43-4 plasmid were grown as in A. Control cells were left untreated, with other cells treated with the DMSO control, 1 uM DOX or 2.5 uM M2I-1. A void was created in the cell lawn and the number of cells that entered the void were scored as above. This experiment was repeated 4 times. This experiment was also repeated 4 times in an independently generated stable C43-4 cell line with similar results. The error of the mean is shown. C. WT and MDA-MB-231 cells stably expressing the C2-4B peptide plasmid were used for the scratch assay as described above. D. WT and MDA-MB-231 cells stably expressing the C13-3 peptide plasmid were used for the scratch assay as described above. The experiments in C and D were only performed once.

FIG. 25 shows the C43-4-FITC/TAT2 complex enters MDA-MB-231 cells, resensitizes them to DOX, activates the APC, and stalls the growth of tumors in mice. A. A weakly toxic dose of 0.1 mg/ml C43-4-FITC/TAT2 complex localizes within nuclei. FITC and DAPI signals are visualized. All cells were imaged with the same settings and magnification. B. Using 0.1 mg/ml C43-4-FITC, weak toxicity is only observed when combined with TAT2, which is worsened with DOX. An equal number of cells were treated with TAT2 and C43-4-FITC alone or in complex, +/−0.5 uM DOX. 24 hours later, 4 random fields of cells were counted and combined. C. MDA-MB-231 cells were treated with 0.001 mg/ml peptide/TAT2 complex for 12 hours, or left untreated. Lysates were prepared and assessed with the antibodies shown. Cyclin B—APC substrate; the PARP 29 kD cleavage fragment is an early sign of apoptosis; induction of total PARP indicates DNA damage; TFPI1 is a nucleolar MDR marker. D. Mice growing MDA-MB-231 cells stably expressing pcDNA-C43-4, injected or left untreated, with the C43-4-FITC/TAT2 complex (n=2 each). 100 ul of 0.01 mg/ml C43-4-FITC peptide was mixed with 25 ul of 1 mg/ml TAT2. The entire 125 ul was given to the mouse using an intraperitoneal (IP) injection. 1 injection/mouse was given in this experiment.

FIG. 26 shows peptides that bind to the APC result in APC activation and synergize with the anti-cancer drug Doxorubicin. A. TNBC MDA-MB-231 cells stably expressing APC binding peptides activate the APC. Cells were grown to confluence and then used to prepare protein lysates. The lysates were used to measure levels of the APC substrate CDC20, which will be reduced if the APC is activated. Cells stably expressing the pcDNA empty vector were used as a control. B. In a similar experiment, MDA-MB-231 cells stably expressing the APC binding peptides shown, or the empty vector control, were used to measure protein levels of the APC substrate HURP using Westerns. C. Triplicate blots as in B were scanned, normalized to tubulin and plotted. Error of the mean is shown. Significant changes are indicated. D. MDA-MB-231 cells stably expressing the empty pcDNA vector, or the C43-4 and C13-3 APC binding peptides, were treated with 1 μM Doxorubicin for 24 hrs. Cell viability was measured using an MTT viability assay.

Figure 27:
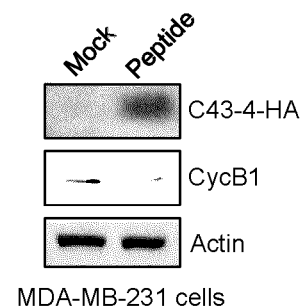

FIG. 27 shows that the HA tagged C43-4 peptide fused to the thioredoxin backbone can be detected using antibodies against HA. As a control, Cyclin B1 levels were also measured and actin was used as a load control. Mock treated cells were also included as a control to show the specificity of the HA band. The HA band migrates at the expected 34 kD.

DESCRIPTION OF VARIOUS EMBODIMENTS

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligonucleotide or polynucleotide chemistry and hybridization described herein are those well-known and commonly used in the art (see, e.g. Green and Sambrook, 2012).

Terms of degree such as "about", "substantially", and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used herein, the terms "subject" and "animal" include all members of the animal kingdom that comprise an anaphase promoting complex. In one embodiment, the subject is a mammal. In another embodiment, the subject is a fish or a bird. In a further embodiment, the subject is a human being.

The term "a cell" includes a single cell as well as a plurality or population of cells. Cells contemplated with the present disclosure include mammalian cells, cancer cells and tumour cells.

Methods and Uses

The present disclosure shows that an activator of the Anaphase Promoting Complex (APC) (M2I-1), reduced the levels of APC substrates in drug-resistant breast cancer cells in culture, sensitized cancer cells to a chemotherapeutic and stalled tumour growth in a mouse model of triple negative breast cancer. The present disclosure also shows that the expression of peptide C43-4 in human breast cancer cells activates the APC and sensitizes the cells to doxorubicin. Further, the 20 amino acid C43-4 peptide, when complexed with the cell permeable TAT2 peptide, enters triple negative breast cancer MDA-MB-231 cells, resensitizes them to doxorubicin, activates the APC, and stalls the growth of tumors in mice.

Accordingly, the disclosure provides a use of an APC activator for treating cancer in a subject in need thereof. Also provided is a method of treating cancer in a subject in need thereof by administering an APC activator to the subject. In another embodiment, an effective amount of an APC activator is used for treating cancer in a subject in need thereof. In another embodiment, an APC activator is used in the preparation of a medicament for treating cancer in a subject in need thereof.

As used herein, the phrase "treating cancer" refers to inhibiting of cancer cell replication, preventing transformation of a cell to a cancer-forming cell, inhibiting of cancer spread (metastasis), inhibiting of tumor growth, reducing cancer cell number or tumor growth, decreasing in the malignant grade of a cancer (e.g., increased differentiation), or improving one or more cancer-related symptoms.

The disclosure further provides a use of an APC activator for reducing resistance to a cancer treatment in a subject or a cancer cell. Also provided is a method of reducing resistance to a cancer treatment in a subject by administering an APC activator to the subject or a cancer cell. In another embodiment, an effective amount of an APC activator is used for reducing resistance to a cancer treatment in a subject or a cancer cell. In another embodiment, an APC activator is used in the preparation of a medicament for reducing resistance to a cancer treatment in a subject or a cancer cell.

The disclosure further provides a use of an APC activator for increasing sensitivity to a cancer treatment in a subject or a cancer cell. Also provided is a method of increasing sensitivity to a cancer treatment in a subject by administering an APC activator to the subject or a cancer cell. In another embodiment, an effective amount of an APC activator is used for increasing sensitivity to a cancer treatment in a subject or a cancer cell. In another embodiment, an APC activator is used in the preparation of a medicament for increasing sensitivity to a cancer treatment in a subject or a cancer cell.

As used herein, the term "resistance" refers to the relative susceptibility of a cancer or a cancer cell to the effects of a cancer treatment. The more resistant a cancer or a cancer cell is to a cancer treatment, the more cancer treatment is required to treat and/or inhibit growth of the cancer or cancer cell. Resistance to a cancer treatment can be acquired through exposure of the cancer to the treatment. Accordingly, the phrase "reducing resistance to a cancer treatment" refers to decreasing the amount of a cancer treatment needed to treat the subject or treat or inhibit growth of the cancer or cancer cell compared to a subject, cancer or cancer cell which was not been administered or contacted with the APC activator. Optionally, the cancer or cancer cell is a cancer or cancer cell that has acquired resistance to a cancer treatment.

As used herein, the term "sensitivity" refers to the relative susceptibility of a cancer or a cancer cell to the effects of a cancer treatment. The more sensitive a cancer or a cancer cell is to a cancer treatment, the more cancer treatment is required to treat and/or inhibit growth of the cancer or cancer cell. Accordingly, the phrase "increasing sensitivity to a cancer treatment" refers to decreasing the amount of a cancer treatment needed to treat the subject or treat or inhibit growth of the cancer or cancer cell compared to a subject, cancer or cancer cell which was not been administered or contacted with the APC activator.

As used herein, the term "cancer treatment" refers to a treatment used to treat, control, or cure a cancer or symptoms thereof. Examples of cancer treatments include, but are not limited to, chemotherapy, radiation, and biologics. In one embodiment, the cancer treatment is a chemotherapeutic. Examples of chemotherapeutics include, but are not limited to agents used to treat breast cancer, lymphoma or leukemia.

The disclosure also provides a use of an APC activator for inhibiting the growth of a cancer cell. Also provided is a method of inhibiting the growth of a cancer cell by contacting the cancer cell with an effective amount of an APC activator. In another embodiment, an effective amount of an APC activator is used for inhibiting the growth of a cancer cell. In another embodiment, an APC activator is used in the preparation of a medicament for inhibiting the growth of a cancer cell. The rate of growth or proliferation of the cancer cell is optionally inhibited by at least 5, 10, 15, 25, 50, 75 or 100% compared to a cancer cell which is not contacted with an APC activator.

As used herein, the term "anaphase promoting complex (APC)" refers to a large evolutionarily conserved complex found in yeast and human . The APC is a ubiquitin protein ligase required for mitotic progression and G1 maintenance. The APC is also necessary for stress response, chromatin assembly, histone biogenesis and longevity in yeast (Harkness et al, 2004; Postnikoff et al, 2012; Harkness et al, 2002; Turner et al, 2010).

As used herein, the term "activator of the Anaphase Promoting Complex (APC)" or "APC activator" refers to a substance that increases the activity of the Anaphase Promoting Complex, measurable for example by a decrease in an APC substrate or multiple APC substrates.

Suitable APC activators include APC activators that decreases the level of at least one APC substrate by at least 10%, at least 20%, at least 30%, at least 40%, at least 50%, at least 60%, at least 70% or at least 80% in the cancer cell compared to a cell not contacted, introduced or a subject not administered the activator.

As used herein, the term "APC substrate" refers to a protein that is degraded by the APC. Examples of APC substrates include, but are not limited to, securin, cyclin B1, HURP, CDC20, PTTG1 and DLGAP5. The "level" of an APC substrate is optionally a mRNA or protein level, which can be assayed by any means known in the art.

Suitable APC activators also include APC activators that increase the cell viability of an wild-type and/or an APC mutant cell by at least 10%, at least 20%, at least 30%, at least 40%, at least 50%, at least 60%, at least 70% or at least 80% compared to a cell with wild-type APC function. As used herein, the expression "increases the viability of an APC mutant" refers to increasing the cell viability of a cell with defective APC function. Examples of yeast cells with defective APC function include apc5 and apc10 mutants. An example of an apc5 mutant is the apc5 temperature sensitive mutant described herein. An example of an apc10 mutant is the apc10 deletion mutant described herein. Viability of a yeast mutant can be measured for example, by the spot dilution assays described herein or any other method known in the art.

As used herein, the expression "binds to the APC" refers to a peptide that binds to at least one subunit of the APC, for example Apc5 or Apc10. Binding can be measured for example, by any method known in the art, including, but not limited to a yeast 2-hybrid assay.

APC substrate expression levels are commonly elevated in cancer. See for example FIG. 16 of the present disclosure which shows that APC substrates are elevated in all 24 cancers analyzed. As defective APC function and/or levels appear to be a general feature in cancer progression and/or onset, without being bound by theory, the APC activators of the present disclosure are useful for treating different cancers.

Accordingly, in one embodiment, the cancer is a cancer which is characterized by defective APC function and/or levels. As used herein, a cancer cell which is "characterized by defective APC function and/or levels" refers to a cancer cell which has decreased function and or amount of APC relative to a non cancer cell. Defective APC function and/or levels can be evidenced, for example, by elevated levels of at least one APC substrate compared to normal tissue. Accordingly, in another embodiment, the cancer is a cancer where at least one APC substrate, for example PTTG1 or DLGAP5, is elevated compared to normal tissue, for example normal adjacent tissue, or suitable non-cancer comparator, optionally wherein the level is assessed by measuring mRNA expression. Expression of APC substrates may be determined, for example, by measuring mRNA or protein expression levels of the substrate.

In one embodiment, the cancer is breast cancer, optionally ER+ breast cancer, ER/PR+ breast cancer, HER2+ breast cancer or "triple negative" breast cancer (ER/PR− HER2− breast cancer). In another embodiment, the cancer is lymphoma, optionally Hodgkin or non-Hodgkin lymphoma or leukemia.

In another embodiment, the cancer cell is optionally a breast cancer cell, optionally ER+ breast cancer cell, ER/PR+ breast cancer cell, HER2+ breast cancer cell or "triple negative" breast cancer cell (ER/PR− HER2− breast cancer cell). In another embodiment, the cancer cell is a lymphoma cell, optionally Hodgkin or non-Hodgkin lymphoma or leukemia cell.

In a further embodiment, the cancer is a cancer resistant to at least one chemotherapeutic, for example a breast cancer, lymphoma or leukemia resistant to at least one chemotherapeutic. Examples of chemotherapeutics for which resistance can develop in cancer cells include, but are not limited to, doxorubicin, rapamycin, capecitabine, carboplatin, cyclophosphamide, gemcitabine, paclitaxel, vinorelbine and tamoxifen. In a further embodiment, the cancer cell is a cancer cell that is resistant to at least one chemotherapeutic.

APC activators include, but are not limited to, small molecules and biologics (for example, peptides, proteins, nucleic acids, antibodies).

The APC activator is optionally a direct or an indirect activator.

In one embodiment, the APC activator is Mad2 Inhibitor-1 (M2I-1). M2I-1 is a commercially available small molecule APC activator that binds to MAD2 and disrupts the interaction between the Spindle Assembly Checkpoint (SAC) component MAD2 and CDC20, an APC co-activator. The disruption of this interaction causes the APC to become activated earlier than usual. In another embodiment, the APC activator is TTKi, which, similar to M2I-1, disrupts the interaction between the SAC component MPS1 and CDC20. In a further embodiment, the APC activator is metformin.

Figure 3A:
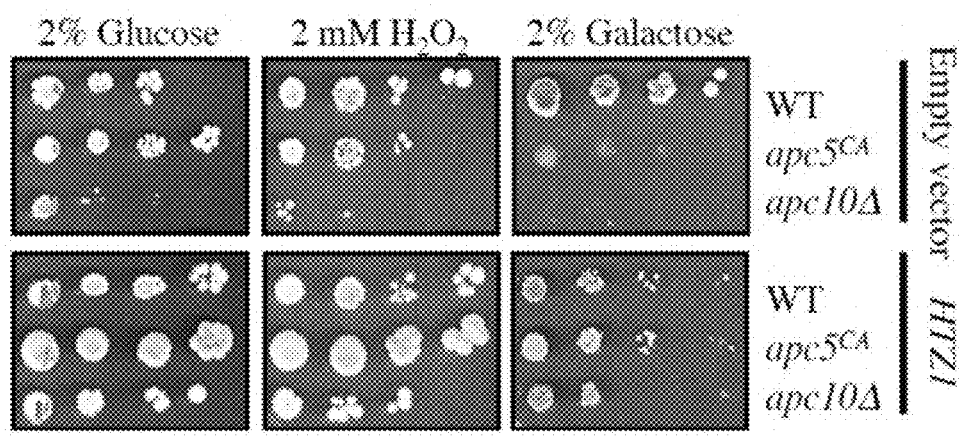

As shown in FIG. 3A, yeast protein histone H2A.Z (Htz1) is an APC activator. Accordingly, in another embodiment, the APC activator is (a) Htz1, (b) a fragment of Htz1 which has the at least the same APC activator activity as Htz1 (for example, increases the viability of a cell with defective APC function or activity and/or binds the APC), (c) a protein or fragment having at least 30, 40, 50, 60, 70, 80, 90, 95 or 98% sequence identity with (a) or (b), or (d) a conservatively substituted variant of (a) or (b). In one embodiment, Htz1 is *Saccharomyces cerevisiae* Htz1. Sequences for Htz1, and the gene encoding Htz1 can be found, for example in online databases such as UniProt and GenBank.

In one embodiment, the APC activator is a compound that comprises or is a peptide. Suitable peptides include peptides that increase the viability of cells with defective anaphase promoting complex (APC) function and/or specifically bind the APC. Examples of peptides that increase the viability of cells with defective anaphase promoting complex (APC) function and/or specifically bind the APC are set out in Tables 1 and 2 (SEQ ID NOs: 1-16).

As used herein, the term "peptide" refers to two or more amino acids linked by a peptide bond, and includes synthetic and natural peptides as well as peptides that are modified. Various lengths of peptides are contemplated herein.

The peptide can for example be 3-50 amino acids in length, optionally 7-30 amino acids in length or at least 25 or 30 amino acids in length. The peptide can for example be any number of amino acids between 3 and 50 including 3 and 50. In one embodiment, the peptide has a maximum length of 30, 35, 40, 45 or 50 amino acids.

Accordingly, in one embodiment, the peptide comprises an amino acid sequence as shown in any one of SEQ ID NOs: 1-16, or a conservatively substituted variant thereof.

Also provided is a peptide that is a part of a sequence described herein, optionally a part of any one of SEQ ID NO: 1-16.

The term "part" with reference to amino acids means at least 5 contiguous amino acids of the reference sequence and up to the reference sequence -1 amino acids. The reference sequence can for example by any one of SEQ ID NO: 1-16, or a conservatively substituted variant thereof.

In another embodiment, the peptide consists essentially of, or consists of an amino acid sequence as shown in any one of SEQ ID NOs: 1-16, or a conservatively substituted variant thereof.

In another embodiment, the peptide comprises at least 30, 40, 50, 60, 70, 80, 90 or 95% sequence identity with the amino acid sequence as shown in any one of SEQ ID NOs: 1-16 or a part thereof. In another embodiment, the peptide comprises or consists of an amino acid sequence comprising at least 5, 6, 7 or 8 contiguous amino acids of SEQ ID NOs: 1-16.

In one embodiment, the peptide has the amino acid sequence set out in SEQ ID NO: 1 (peptide "C43-4"). Peptide "C43-4" binds Apc10 in a yeast 2 hybrid assay and increases the viability of WT cells, and of an APC mutant. Residues 2-14 of SEQ ID NO: 1 (SEQ ID NO: 12) have homology with histone variant Htz1 in yeast (human H2AZ).

In another embodiment, the peptide has at least 50, 60, 70, 80, 90 or 95% sequence identity with GSSHNDLRVRRLT (SEQ ID NO: 12) or NGSSHNDLRVRRLTLISRLC (SEQ ID NO: 1). In another embodiment, the peptide comprises at least 5, 6, 7 or 8 contiguous amino acids of GSSHNDLRVRRLT (SEQ ID NO: 12) or NGSSHNDLRVRRLTLISRLC (SEQ ID NO: 1). In another embodiment, the peptide comprises or consists of GSSHNDLRVRRLT (SEQ ID NO: 12) or NGSSHNDLRVRRLTLISRLC (SEQ ID NO: 1). In a further embodiment, the peptide comprises an amino acid sequence that has at least 30, 40, 50, 60, 70, 80, 90 or 95% sequence identity with a corresponding Htz1 fragment. In another embodiment, the peptide has at least 50, 60, 70, 80, 90 or 95% sequence identity with GSSHNDLRVRRLT (SEQ ID NO: 12) or NGSSHNDLRVRRLTLISRLC (SEQ ID NO: 1) and/or comprises at least 5, 6, 7 or 8 contiguous amino acids of GSSHNDLRVRRLT (SEQ ID NO: 12) or NGSSHNDLRVRRLTLISRLC (SEQ ID NO: 1, wherein the peptide increases the resistance of a yeast cell to stress such as UV light exposure. Increased resistance of a yeast cell to UV light exposure can be measured for example, by the spot dilution assay described herein or any other method known in the art.

Mutating residues 7, 12 and 14 of SEQ ID NO: 1 resulted in a loss of peptide function. Thus, in another embodiment, the peptide comprises or consists of amino acid sequence XSSHXDAXXXRXT (SEQ ID NO: 24), wherein X is any amino acid and the peptide optionally has a maximum length of 30 amino acids, or a conservatively substituted variant thereof. In a further embodiment, the peptide comprises or consists of amino acid sequence XSSHXDAXXXRXT (SEQ ID NO: 24), wherein the peptide increases the resistance of a yeast cell to stress such as UV light exposure. Increased resistance of a yeast cell to UV light exposure can be measured for example, by the spot dilution assays described herein or any other method known in the art. In another embodiment, In another embodiment, the peptide comprises or consists of amino acid sequence GSSHNDARVRRLT (SEQ ID NO: 25), or a conservatively substituted variant thereof.

A variant of peptide "C43-4" is also provided, wherein the leucine residue at position 8 of SEQ ID NO: 1 is replaced with alanine (SEQ ID NO: 2) (peptide "C43-4-3"). Peptide "C43-4-3" binds Apc10 in a yeast 2 hybrid assay. Thus, in another embodiment, the peptide comprises or consists of amino acid sequence NGSSHNDARVRRLTLISRLC (SEQ ID NO: 2), or a conservatively substituted variant thereof. In one embodiment, the peptide has an alanine residue at the amino acid corresponding to position 8 of SEQ ID NO: 2. In another embodiment, the peptide does not have an leucine residue at the amino acid corresponding to position 8 of SEQ ID NO: 2.

As used herein, the term "conservatively substituted variant" refers to a variant with at least one conservative amino acid substitution. A "conservative amino acid substitution" as used herein, refers to the substitution of an amino acid with similar hydrophobicity, polarity, and R-chain length for one another. In a conservative amino acid substitution, one amino acid residue is replaced with another amino acid residue without abolishing the protein's desired properties. Without the intention of being limited thereby, in one embodiment, the substitutions of amino acids are made that preserve the structure responsible for the ability to increase the viability of a cell with defective APC function and/or bind to the APC as disclosed herein. Examples of conservative amino acid substitutions include:

| Conservative Substitutions | |
|---|---|
| Type of Amino Acid | Substitutable Amino Acids |
| Hydrophilic | Ala, Pro, Gly, Glu, Asp, Gln, Asn, Ser, Thr |
| Sulphydryl | Cys |
| Aliphatic | Val, Ile, Leu, Met |
| Basic | Lys, Arg, His |
| Aromatic | Phe, Tyr, Trp |

In one embodiment, the peptide has the amino acid sequence set out in SEQ ID NO: 4 (peptide "C2-4B"). Peptide "C2-4B" binds Apc10 in a yeast 2 hybrid assay and increases the viability of an APC mutant. C2-4B has homology with Sum1 in yeast. Thus, in another embodiment, the peptide has an amino acid sequence that has at least 30, 40, 50, 60, 70, 80, 90, 95 or 98% sequence identity with a corresponding fragment of Sum1.

Thus, in another embodiment, the peptide has at least 50, 60, 70, 80, 90, 95 or 98% sequence identity with RMPQWWQWM (SEQ ID NO: 14) or RMPQWWQWMWV (SEQ ID NO: 4). In another embodiment, the peptide comprises at least 5, 6, 7 or 8 contiguous amino acids of RMPQWWQWM (SEQ ID NO: 14) or RMPQWWQWMWV (SEQ ID NO: 4). In another embodiment, the peptide comprises or consists of RMPQWWQWM (SEQ ID NO: 14) or RMPQWWQWMWV (SEQ ID NO: 4) or a conservatively substituted variant thereof.

In one embodiment, the peptide comprises or consists of the amino acid sequence set out in SEQ ID NO. 3 (peptide "C9-5"). This peptide binds Apc5 in a yeast 2 hybrid assay and increases the viability of an APC mutant. Residues 5-19 of SEQ ID NO: 3 (SEQ ID NO: 13) have homology with Swe1 in yeast (human Wee1).

Thus, in another embodiment, the peptide comprises amino acid sequence ETETFHPITRHLIVP (SEQ ID NO: 13) or a conservatively substituted variant thereof and the peptide optionally has a maximum length of 30 amino acids. In another embodiment, the peptide comprises or consists of amino acid sequence CECLETETFHPITRHLIVPV (SEQ ID NO: 3), or a conservatively substituted variant thereof. In another embodiment, the peptide has at least 50, 60, 70, 80, 90 or 95% sequence identity with ETETFHPITRHLIVP (SEQ ID NO: 13) or CECLETETFHPITRHLIVPV (SEQ ID NO: 3). In yet another embodiment, the peptide comprises at least 5, 6, 7, or 8 contiguous amino acids of ETETFHPITRHLIVP (SEQ ID NO: 13) or CECLETETFHPITRHLIVPV (SEQ ID NO: 3). In another embodiment, the peptide comprises an amino acid sequence that has at least 30, 40, 50, 60, 70, 80, 90 or 95% sequence identity with a corresponding fragment of Swe1.

In one embodiment, the peptide comprises or consists of the amino acid sequence set out in SEQ ID NO: 5 (peptide "C3-1"). This peptide binds Apc10 in a yeast 2 hybrid assay and increases the viability of an APC mutant.

Thus, in another embodiment, the peptide comprises or consists of PSYNTIKYHETHGGRHPRRQPKRPI (SEQ ID NO: 5), or a conservatively substituted variant thereof. In another embodiment, the peptide has at least 50, 60, 70, 80, 90, 95 or 98% sequence identity with PSYNTIKYHETHGGRHPRRQPKRPI (SEQ ID NO: 5). In yet another embodiment, the peptide comprises at least 5, 6, 7, or 8 contiguous amino acids of PSYNTIKYHETHGGRHPRRQPKRPI (SEQ ID NO: 5).

In one embodiment, the peptide has the amino acid sequence set out in SEQ ID NO. 6 (peptide "C13-3"). This peptide binds Apc5 in a yeast 2 hybrid assay and increases the viability of an APC mutant. This peptide has homology with yeast proteins Mad2, Hxt2 and/or Ubc7.

Accordingly, in another embodiment, the peptide comprises or consists of GALKEVCICIVESVGGEVFS (SEQ ID NO: 6), or a conservatively substituted variant thereof. In another embodiment, the peptide has at least 50, 60, 70, 80, 90, 95 or 98% sequence identity with GALKEVCICIVESVGGEVFS (SEQ ID NO: 6). In yet another embodiment, the peptide comprises at least 5, 6, 7, or 8 contiguous amino acids of GALKEVCICIVESVGGEVFS (SEQ ID NO: 6). In another embodiment, the peptide comprises an amino acid sequence that has at least 30, 40, 50, 60, 70, 80, 90, 95 or 98% sequence identity with a corresponding fragment of Mad2, Hxt2 and/or Ubc7.

In one embodiment, the peptide has the amino acid sequence set out in SEQ ID NO: 7 (peptide "C24-1"). This peptide binds Apc5 in a yeast 2 hybrid assay and increases the viability of an APC mutant. The following motifs of interest were also identified: SKWT (SEQ ID NO: 46) and MCMS (SEQ ID NO: 47).

Thus, in one embodiment, the peptide comprises the amino acid motifs SKWT (SEQ ID NO: 46) and MCMS (SEQ ID NO: 47) and the peptide optionally has a maximum length of 30 amino acids. In another embodiment, the peptide comprises or consists of SKWTWRMCMS (SEQ ID NO: 48), or a conservatively substituted variant thereof. In another embodiment, the peptide comprises or consists of SKWTWRMCMSWTVDRFAPVPWP (SEQ ID NO: 7), or a conservatively substituted variant thereof. In another embodiment, the peptide has at least 50, 60, 70, 80, 90, 95 or 98% sequence identity with SKWTWRMCMSWTVDRFAPVPWP (SEQ ID NO: 7). In yet another embodiment, the peptide comprises at least 5, 6, 7, or 8 contiguous amino acids of SKWTWRMCMSWTVDRFAPVPWP (SEQ ID NO: 7).

In one embodiment, the peptide has the amino acid sequence set out in SEQ ID NO: 8 (peptide "C1-8").

Thus, in one embodiment, the peptide comprises or consists of FCL (SEQ ID NO: 8), or a conservatively substituted variant thereof is provided. In another embodiment, the peptide has at least 66% sequence identity with FCL (SEQ ID NO: 8).

In one embodiment, the peptide has the amino acid sequence set out in SEQ ID NO: 9 (peptide "C50-1"). This peptide binds Apc10 in a yeast 2 hybrid assay and increases the viability of an APC mutant.

Thus, in one embodiment, the peptide comprises or consists of RRCLSIRTENLAWEGKFLRV (SEQ ID NO: 9), or a conservatively substituted variant thereof is provided. In another embodiment, the peptide has at least 50, 60, 70, 80, 90, 95 or 98% sequence identity with RRCLSIRTENLAWEGKFLRV (SEQ ID NO: 9). In yet another embodiment, the peptide comprises at least 5, 6, 7, or 8 contiguous amino acids of RRCLSIRTENLAWEGKFLRV (SEQ ID NO: 9).

In one embodiment, the peptide has the amino acid sequence set out in SEQ ID NO: 15 (peptide "C3-1B"). This peptide binds Apc10 in a yeast 2 hybrid assay.

Thus, in one embodiment, the peptide comprises or consists of PVNGERWAP (SEQ ID NO: 15), or a conservatively substituted variant thereof is provided. In another embodiment, the peptide has at least 50, 60, 70, 80, 90, 95 or 98% sequence identity with PVNGERWAP (SEQ ID NO: 15). In yet another embodiment, the peptide comprises at least 5, 6, 7, or 8 contiguous amino acids of PVNGERWAP (SEQ ID NO: 15).

In one embodiment, the peptide has the amino acid sequence set out in SEQ ID NO: 16. Thus, in another embodiment, the peptide comprises or consists of GRMLMTYLMYFMVLWVPRPWGPPL (SEQ ID NO: 16), or a conservatively substituted variant thereof. In another embodiment, the peptide has at least 50, 60, 70, 80, 90, 95 or 98% sequence identity with GRMLMTYLMYFMVLWVPRPWGPPL (SEQ ID NO: 16). In yet another embodiment, the peptide comprises at least 5, 6, 7, or 8 contiguous amino acids of GRMLMTYLMYFMVLWVPRPWGPPL (SEQ ID NO: 16).

In one embodiment, peptides that rescue apc5 temperature sensitive (ts) growth but do not bind the APC are provided. Two of examples of these peptides are identified as "Y65" and "Y36" in the present disclosure.

Accordingly, in one embodiment, the peptide has the amino acid sequence set out in SEQ ID NO: 10 (peptide "Y65"). This peptide increases the viability of an apc5 temperature sensitive (ts) growth mutant. This peptide has homology with yeast protein Elc1.

Thus, in one embodiment, a peptide having at least 50, 60, 70, 80, 90, 95 or 98% sequence identity with VRQKSDKEYERVLGLGLRR (SEQ ID NO: 10) is provided. In one embodiment, the peptide increases the viability of an apc5 temperature sensitive (ts) growth mutant, and has a maximum length of 30 amino acids. In another embodiment, the peptide comprises or consists of VRQKSDKEYERVLGLGLRR (SEQ ID NO: 10), or a conservatively substituted variant thereof. In another embodiment, the peptide has at least 50, 60, 70, 80, 90, 95 or 98% sequence identity with VRQKSDKEYERVLGLGLRR (SEQ ID NO: 10). In yet another embodiment, the peptide comprises at least 5, 6, 7, or 8 contiguous amino acids of VRQKSDKEYERVLGLGLRR (SEQ ID NO: 10). In a further embodiment, the peptide comprises an amino acid sequence that has at least 30, 40, 50, 60, 70, 80, 90, 95 or 98% sequence or identity with Elc1 or a fragment thereof.

In one embodiment, the peptide has the amino acid sequence set out in SEQ ID NO: 11 (peptide "Y36") is also provided. This peptide increases the viability of an apc5 temperature sensitive (ts) growth mutant. This peptide has homology with yeast proteins Tim17, Sit4, Im13, Scc4 (cohesin complex) and Ngs1.

Thus, in one embodiment, the peptide has at least 50, 60, 70, 80, 90, 95 or 98% sequence identity with SWLNGSGGWLWLFSNFCCG (SEQ ID NO: 11). In one embodiment, the peptide increases the viability of an apc5 temperature sensitive (ts) growth mutant, and has a maximum length of 30 amino acids. In another embodiment, the peptide comprises or consists of SWLNGSGGWLWLFSNFCCG (SEQ ID NO: 11), or a conservatively substituted variant thereof. In another embodiment, the peptide has at least 50, 60, 70, 80, 90, 95 or 98% sequence identity with SWLNGSGGWLWLFSNFCCG (SEQ ID NO: 10). In yet another embodiment, the peptide comprises at least 5, 6, 7, or 8 contiguous amino acids of SWLNGSGGWLWLFSNFCCG (SEQ ID NO: 10). In a further embodiment, the peptide comprises an amino acid sequence that has at least 30, 40, 50, 60, 70, 80, 90, 95 or 98% sequence identity with Tim17, Sit4, Im13, Scc4 and/or Ngs1 or a fragment thereof.

In one embodiment, peptides having at least 30, 40, 50, 60, 70, 80, 90 or 95% sequence identity with SEQ ID NOs: 1-16 have the same function and/or activity as peptides comprising or consisting of SEQ ID NOs: 1-16.

Sequence identity can be calculated according to methods known in the art. Sequence identity is most preferably assessed by the algorithm of BLAST version 2.1 advanced search. BLAST is a series of programs that are available, for example, online from the National Institutes of Health. The advanced blast search is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131_141; Altschul, S. F., Madden, T. L., Schïffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L. (1997) "PowerBLAST: A new network BLAST application for interactive or automated sequence analysis and annotation." Genome Res. 7:649656. In addition, percent identity or homology between two sequences may be determined by comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

One or more amino acid insertions may be introduced into the amino acid sequences shown in SEQ ID NOs: 1-16. Amino acid insertions may consist of single amino acid residues or sequential amino acids ranging from 2 to 15 amino acids in length.

Deletions may consist of the removal of one or more amino acids, or discrete portions from the amino acid sequence shown in SEQ ID NOs: 1-16. The deleted amino acids may or may not be contiguous. The lower limit length of the resulting analog with a deletion mutation is at least 6, 7 or 8 amino acids.

Exemplary methods of making the alterations set forth above are disclosed by Sambrook et al (Molecular Cloning: A Laboratory Manual, 2nd Ed., Cold Spring Harbor Laboratory Press, 1989).

In one embodiment, the peptides described herein are modified for cell permeability, improved stability, and better bioavailability. These modifications may include, without limitation, peptide conjugation, peptide cyclization, peptide end modification (e.g. N-acetylation or C-amidation), side chain modifications including the incorporation of non-coded amino acids or non-natural amino acids, N-amide nitrogen alkylation, chirality changes (incorporation of or replacement of L-amino acids with D-amino acids), generation of pseudopeptides (e.g. amide bond surrogates), peptoids, azapeptides or azatides.

In one embodiment, the peptides described herein are conjugated, directly or indirectly to a moiety which allows the purification, detection, immobilization, and/or cellular targeting of the peptide, and/or which increases the bioavailability, expression and/or stability of the peptide. Accordingly, in one embodiment, the APC activator is a compound comprising a peptide as described herein conjugated to a moiety.

The moiety may be selected from: (i) a cell-penetrating moiety, (ii) a detection moiety such a myc tag, HA-tag, V5-tag or NE-tag, fluorescent protein which is capable of producing, either directly or indirectly, a detectable signal, a radio-opaque, or a radioisotope, such as $^{3}H$, $^{13}N$, $^{14}C$, $^{18}F$, $^{32}P$, $^{35}S$, $^{123}I$, $^{125}I$, $^{131}I$; a fluorescent (fluorophore) or chemiluminescent (chromophore) compound, such as fluorescein isothiocyanate (FITC), rhodamine or luciferin; an enzyme, such as alkaline phosphatase, beta-galactosidase or horseradish peroxidase; an imaging agent; or a metal ion, (iii) a binding moiety such as an epitope tag (polyHis6, FLAG, HA, myc.), a DNA-binding domain, a hormone-binding domain or a poly-lysine tag for immobilization onto a support, (iv) a targeting moiety for addressing the peptide to a specific cell type or cell compartment or (iv) an enhancer moiety that can increase or enhance the activity of the peptide, for example a permeability enhancer, a stability enhancer or a bioavailability enhancer. The moiety may be conjugated to the C or N terminus of the peptide. The peptide may be conjugated directly or indirectly to the moiety.

A peptide as described herein is optionally conjugated to the moiety by a linker sequence. Suitable linker sequences include glycine or serine-rich linker sequences. The linker may also comprise a recognition site for a protease, for example, for removing the moiety from the peptide. Alternatively, the moiety may be conjugated to the peptide by chemical coupling in any suitable manner known in the art, for example by a covalent or non-covalent bond.

In one embodiment, the moiety is a cell-penetrating moiety. As used herein, the term "cell-penetrating moiety" refers to a moiety that promotes cellular uptake of the peptide upon delivery to a target cell. Examples of cell-penetrating moieties include cell-penetrating peptides that translocate across the plasma membrane of eukaryotic cells at higher levels than passive diffusion. In one embodiment, the cell-penetrating peptide can translocate the nuclear membrane of a cell to enter the nucleus. In another embodiment, the cell-penetrating peptide can enter the nucleolus.

In one embodiment, the cell-penetrating peptide is an amphipathic peptide comprising both a hydrophilic (polar) domain and a hydrophobic (non-polar) domain.

Cell-penetrating peptides can include sequences from membrane-interacting proteins such as signal peptides, transmembrane domains and antimicrobial peptides.

Thus, in one embodiment, the cell-penetrating peptide is a peptide that enters the nuclei of a cell.

In one particular embodiment, the cell-penetrating peptide is a TAT peptide derived from the transactivating protein TAT of HIV-1 (amino acids 49-57 of HIV Tat protein; RKKRRQRRRR; SEQ ID NO: 17) or TAT2 (RKKRRQRRRRKKRRQRRR (SEQ ID NO: 26), Rudolph et al. (2003)), or a conservatively substituted variant thereof. TAT2 is a dimer of the TAT monomer.

In another embodiment, the cell-penetrating peptide is Pep1 (KETWWETWWTEWSQPKKKRKV (SEQ ID NO: 27); Henriques et al. (2005)), R9 (RRRRRRRRR (SEQ ID NO: 28); Meloni et al. (2015)), TAT-NBD (TAT-TALDWSWLQTE (SEQ ID NO: 29); Edwards et al. (2018)), Transportan (GWTLNSAGYLLGKINLKA-LAALAKKIL (SEQ ID NO: 30); Pooga et al. (2001)), pVEC (IAARIKLRSRQHIKLRHL (SEQ ID NO: 31); Mae et al. (2005)), the third helix of the homeodomain of antennapedia (penetratin), VP22 and conservatively substituted variants thereof. Other examples of cell-penetrating peptides include polyarginine-based peptides, calcitonin-derived peptides, and oligomers. Further examples of cell-penetrating peptides are described, for example, in Copolovic et al. (2014).

The peptides described herein may be prepared using recombinant DNA methods. These peptides may be purified and/or isolated to various degrees using techniques known in the art. Accordingly, nucleic acid molecules having a sequence which encodes a peptide of the disclosure may be incorporated according to procedures known in the art into an appropriate expression vector which ensures good expression of the peptide. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell" means that the expression vectors contain a nucleic acid molecule encoding a peptide of the disclosure and regulatory sequences, selected on the basis of the host cells to be used for expression, which are operatively linked to the nucleic acid molecule. "Operatively linked" is intended to mean that the nucleic acid is linked to regulatory sequences in a manner which allows expression of the nucleic acid.

Alternatively, the peptides described herein can be prepared by chemical synthesis using techniques well known in the chemistry of proteins such as solid phase synthesis [Merrifield 1964] or synthesis in homogeneous solution [Houbenwycl, 1987].

Various methods of administration of the APC activators described herein are contemplated. In one embodiment, the APC activators are administered or are for use parenterally, e.g. intravenously, intraperitoneally, intradermally, subcutaneously, orally, transdermally (i.e., topically), transnasally, transmucosally, or rectally. In another embodiment, the APC activator is administered directly to the tumour, for example by injection to the tumor.

Where the APC activator is a peptide, the peptide itself may be administered to the subject. In another embodiment, DNA encoding the peptide may be administered to the subject. Suitable vectors are known in the art for administering DNA to subjects. For example, modified viruses including retroviruses and adenoviruses, may be used to administer DNA encoding a peptide to a subject. The vector can be injected or administered intravenously to the subject. Alternately, a sample of the subject's cells can be removed and exposed to the vector in a laboratory setting. The cells containing the vector are then returned to the patient.

The amount required to be administered will depend on the activity of the activator, and will also depend on the rate at which an administered activator is depleted from the free volume of the subject to which it is administered. Common ranges for effective dosing of an APC activator of the disclosure may be, by way of non-limiting example, from about 0.1 mg/kg body weight to about 50 mg/kg body weight. Common dosing frequencies may range, for example, from twice daily to once a week.

Efficaciousness of treatment can be determined in association with any known method for determining the effectiveness of a cancer treatment.

Combinations of compounds comprising different peptides are also contemplated for use in the methods and uses described herein.

The APC activator may be used or administered in combination with at least one additional agent for treating cancer. The additional agent is optionally a therapeutic drug, for example a chemotherapeutic.

As used herein, the term "chemotherapeutic" refers to an agent used to treat, control, or cure a cancer or symptoms thereof. Examples of chemotherapeutics include, but are not limited to agents used to treat breast cancer, lymphoma or leukemia.

In one embodiment, the additional agent is a chemotherapeutic used to treat breast cancer. Chemotherapeutics used to treat breast cancer include, but are not limited to, doxorubicin, rapamycin, capecitabine, carboplatin, cyclophosphamide, gemcitabine, paclitaxel, vinorelbine and tamoxifen. In another embodiment, the additional agent is a chemotherapeutic used to treat lymphoma or a chemotherapeutic used to treat leukemia.

An additional agent may be used or administered prior to, overlapping with, concurrently, and/or after administration of the APC activator. In one embodiment, the APC activator and the additional agent are be used or administered contemporaneously as part of a regimen. When administered concurrently, the activator and an additional agent may be use or administered in a single formulation or in separate formulations, and if administered separately, then optionally, by different modes of administration.

Peptides

The disclosure also provides a peptide comprising amino acid sequence FCL (SEQ ID NO: 8), or a conservatively substituted variant thereof and wherein the peptide optionally has a maximum length of 30 amino acids. In another embodiment, the peptide consists of FCL (SEQ ID NO: 8), or a conservatively substituted variant thereof. In another embodiment, the peptide has at least 66% sequence identity with FCL (SEQ ID NO: 8).

The disclosure also provide a peptide comprising amino acid sequence PVNGERWAP (SEQ ID NO: 15), or a conservatively substituted variant thereof and wherein the peptide optionally has a maximum length of 30 amino acids. In another embodiment, the peptide comprises or consists of PVNGERWAP (SEQ ID NO: 15), or a conservatively substituted variant thereof. In another embodiment, the peptide has at least 50, 60, 70, 80, 90, 95 or 98% sequence identity with PVNGERWAP (SEQ ID NO: 15). In yet another embodiment, the peptide comprises at least 5, 6, 7, or 8 contiguous amino acids of PVNGERWAP (SEQ ID NO: 15).

Compositions

The disclosure also provides a composition, optionally a pharmaceutical composition, comprising an activator of the Anaphase Promoting Complex (APC) as described herein.

In one embodiment, the composition is for use in a method described herein. In an embodiment, the composition comprises a carrier or diluent.

The carrier can optionally be a pharmaceutically acceptable carrier.

As used herein, the term "pharmaceutically acceptable carrier" is intended to include any and all solvents, dispersion media, coatings, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Optional examples of such carriers or diluents include, but are not limited to, water, saline, ringer's solutions, dextrose solution, and 5% human serum albumin and bovine serum albumin (BSA).

In another embodiment, the carrier is a carrier that will protect the APC activator against rapid elimination from the body, such as a sustained/controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

A pharmaceutical composition is formulated to be compatible with its intended route of administration. Examples of routes of administration include parenteral, e.g. intravenous, intraperitoneal, intradermal, subcutaneous, oral, transdermal (i.e., topical), transnasal, transmucosal, or rectal. In one particular embodiment, the pharmaceutical composition is formulated to be compatible with intravenous, intraperitoneal or transnasal administration.

Various concentrations of the APC activators described herein may be prepared for administration. In one embodiment, the composition comprises at least 0.5 mg/ml APC activator, optionally at least 0.75, 1, 2, 5 or 10 mg/ml APC activator. In another embodiment, the composition comprises from 0.1 to 5 mg/ml APC activator, optionally, 0.5 to 1.5 mg/ml APC activator, 0.8 to 1.2 mg/ml APC activator or about 1.0 mg/ml APC activator.

In one embodiment, the composition is formulated in dosage unit form for ease of administration and uniformity of dosage. Dosage unit form as used herein refers to physically discrete units suited as unitary dosages for the subject to be treated; each unit containing a predetermined quantity of active ingredient calculated to produce the desired therapeutic effect in association with a carrier. The specification for the dosage unit forms are dictated by and directly dependent on the unique characteristics of the APC activator and the particular therapeutic effect to be achieved, and the limitations inherent in the art of preparing such an APC activator for the treatment of individuals.

The composition can also contain more than one active ingredient as necessary for the particular indication being treated, optionally those with complementary activities that do not adversely affect each other. Alternatively, or in addition, the composition can comprise an agent that enhances the function of the APC activator, such as, for example, a cytotoxic agent, cytokine, chemotherapeutic, or growth-inhibitory agent. Such molecules are suitably present in combination in amounts that are effective for the purpose intended.

In one particular embodiment, the composition further comprises a chemotherapeutic, optionally a chemotherapeutic used for treating breast cancer such as, but are not limited to, rapamycin, capecitabine, carboplatin, cyclophosphamide, doxorubicin, gemcitabine, paclitaxel, vinorelbine and tamoxifen. In one particular embodiment, the composition further comprises doxorubicin. In another embodiment, the chemotherapeutic is a chemotherapeutic used for treating lymphoma or leukemia.

In a further embodiment, the composition or activator is housed in a delivery vehicle. Any suitable passive or targeted delivery vehicle can be employed including, but not limited to, viral vectors, biodegradable microspheres, microparticles, nanoparticles, liposomes, collagen minipellets, and cochleates.

The disclosure also provides a use of a composition comprising an APC activator as described herein, optionally a peptide, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

Further provided is a composition comprising an APC activator as described herein, optionally a peptide, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure further provides a use of a composition comprising an APC activator as described herein, optionally a peptide comprising or consisting of an amino acid sequence as shown in any one of SEQ ID NOs: 1-16, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in any one of SEQ ID NOs: 1-16, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure further provides a use of a composition comprising an APC activator as described herein, optionally a peptide comprising or consisting of an amino acid sequence as shown in SEQ ID NO: 1, 5 or 6, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in SEQ ID NO: 1, 5 or 6, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in any one of SEQ ID NOs: 1-16, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure further provides a use of a composition comprising an APC activator as described herein, optionally a peptide comprising or consisting of an amino acid sequence as shown in SEQ ID NO: 1, 3, 4, 5, 6 or 15, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in SEQ ID NO: 1, 3, 4, 5, 6 or 15, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure further provides a use of a composition comprising an APC activator as described herein, optionally a peptide comprising amino acid sequence XSSHXDAXXXRXT, wherein X is any amino acid, optionally wherein the amino acid sequence is GSSHNDARVRRLT or an amino acid sequence having at least 50, 60, 70, 80, 90, 95 or 98% sequence identity thereto, and optionally wherein the peptide has a maximum length of 30 amino acids, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising amino acid sequence XSSHXDAXXXRXT, wherein X is any amino acid, optionally wherein the amino acid sequence is GSSHNDARVRRLT or an amino acid sequence having at least 50, 60, 70, 80, 90, 95 or 98% sequence identity thereto, and optionally wherein the peptide has a maximum length of 30 amino acids, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in SEQ ID NO: 1 or 2, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The disclosure also provides a composition comprising an APC activator as described herein, optionally a peptide comprising or consisting of an amino acid sequence as shown in SEQ ID NO: 1 or 2, or a conservatively substituted variant thereof, for treating cancer in a subject, for inhibiting growth of a cancer cell, for increasing sensitivity to a chemotherapeutic in a subject or a cancer cell and/or for reducing resistance to a chemotherapeutic in a subject or cancer cell wherein the cancer is optionally breast cancer, lymphoma or leukemia and the chemotherapeutic is optionally a chemotherapeutic used to treat breast cancer, lymphoma or leukemia.

The above disclosure generally describes the present application. A more complete understanding can be obtained by reference to the following specific examples. These examples are described solely for the purpose of illustration and are not intended to limit the scope of the disclosure. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present disclosure:

EXAMPLES

Example 1

Yeast forward- and reverse-genetic screens were performed to identify small peptides that impact APC function. By definition, a reverse screen can discover the function of a gene using gene/protein specific tools, whereas a forward screen can uncover the genetic basis of a phenotype.

Figure 8:
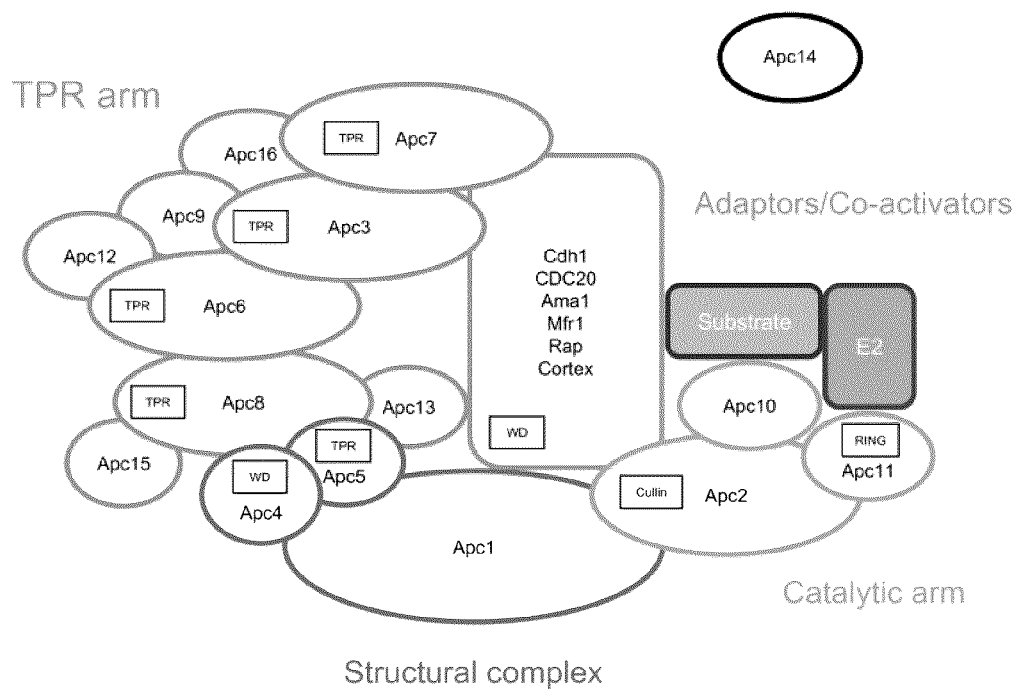

The reverse genetic screen utilized a yeast 2-hybrid (Y2H) protocol that selected for peptides that bound to the APC subunits Apc5 or Apc10 (see FIG. 8 for APC structure), to assess whether peptide-binding might modify APC function. Peptides that bound APC subunits were then assayed for those that suppressed APC mutant defects.

Figure 1A:
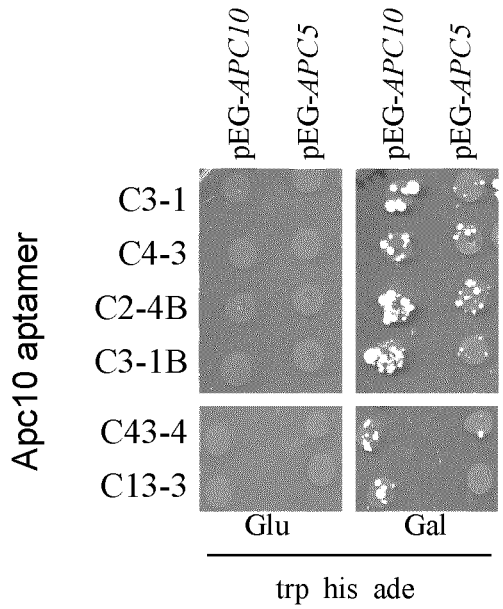

A library of random small peptides were cloned into a Thioredoxin (Trx) scaffold (see FIG. 9 for Trx-peptide structure) and expressed from a galactose-inducible Y2H prey vector in cells expressing the Apc10 bait vector (the modified Apc10 is still part of the complete APC complex). Six peptides that reproducibly interacted with the Apc10 bait construct in Y2H assays were identified (FIG. 1A) and were examined further. Cells will only grow in this assay if the peptide interacts with Apc5 or Apc10.

Figure 1B:
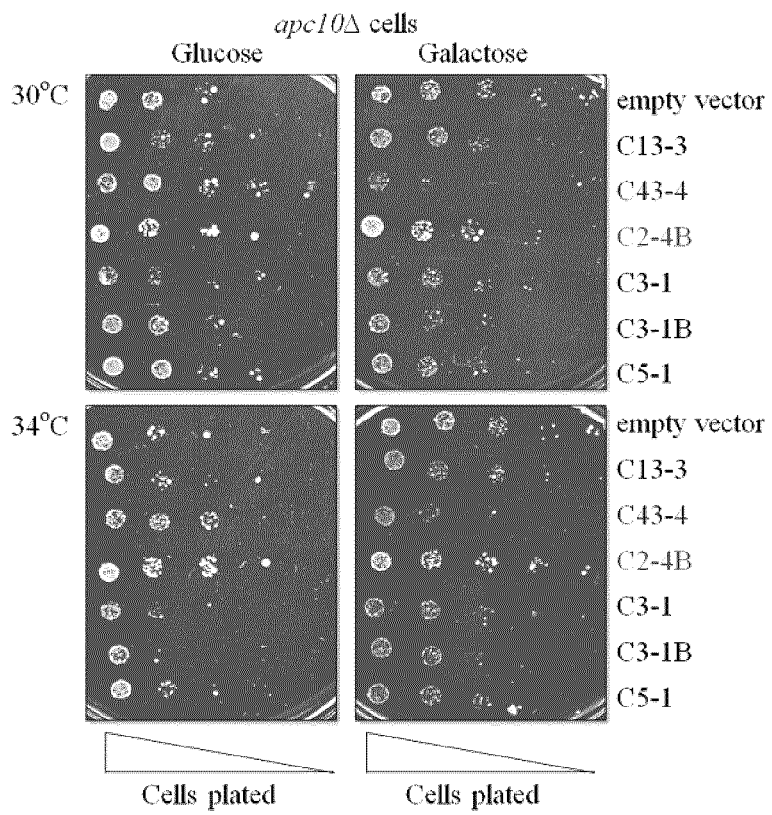
Figure 1C:
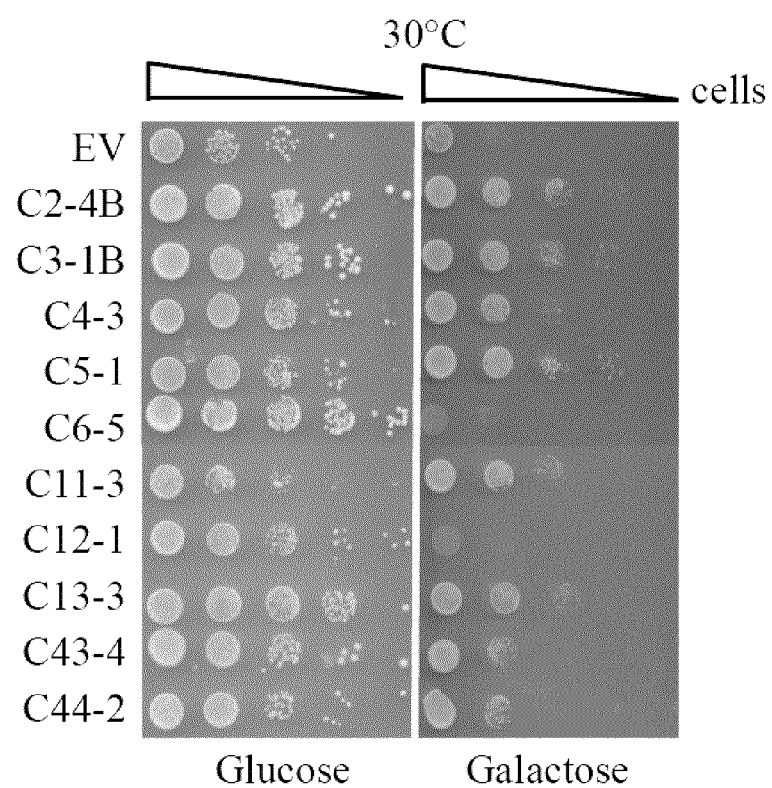
Figure 2A:
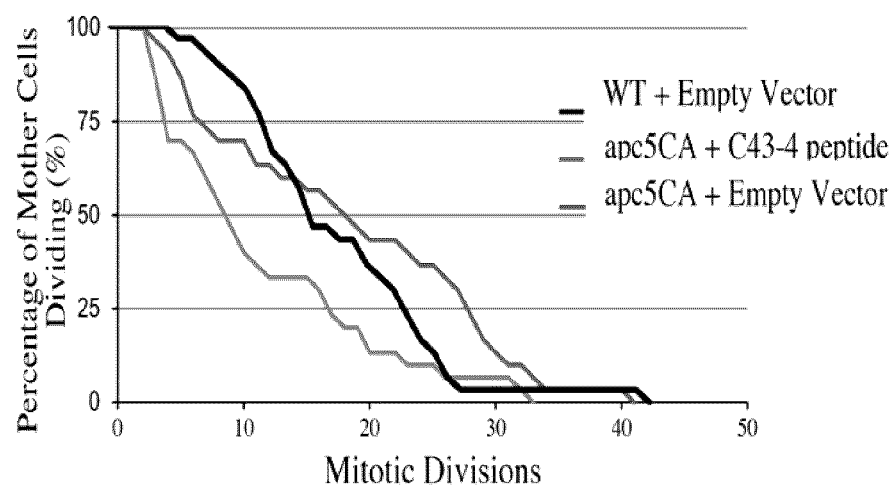
Figure 2B:
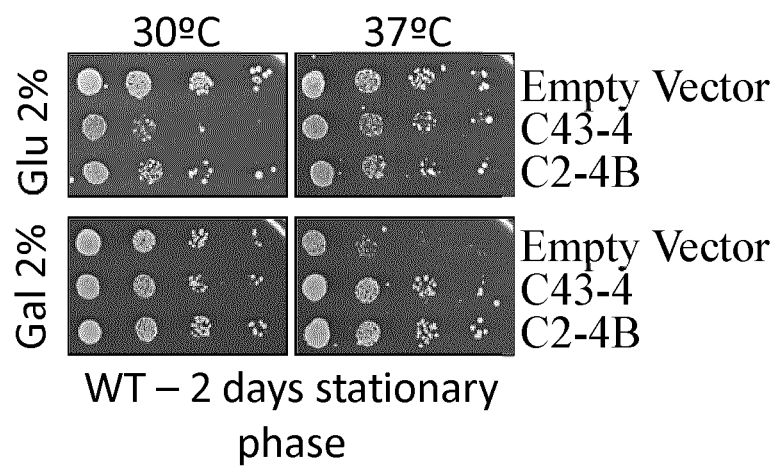

The six peptide expressing vectors were transformed into apc10Δ cells and assessed for temperature sensitive growth. Two of the peptides, C43-4 and C2-4B, suppressed the apc10Δ growth phenotype at 30 and 34° C. when weakly expressed on glucose (FIG. 1B). When expressed in wild type (WT) cells, most of the peptides improved growth (FIG. 1C). C43-4 increased replicative lifespan of apc5$^{CA}$ cells (FIG. 2A), while both C43-4 and C2-4B improved chronological lifespan of WT cells (FIG. 2B). The sequence of the C43-4 peptide shares homology with the yeast gene HTZ1. When HTZ1 was overexpressed in WT yeast cells, increased stress resistance (FIG. 3A) was observed, indicating that C43-4 may mimic the effects of Htz1 on the APC. $H_2O_2$ induces oxidative stress whereas galactose induces a carbon stress.

Figures 5, 6:
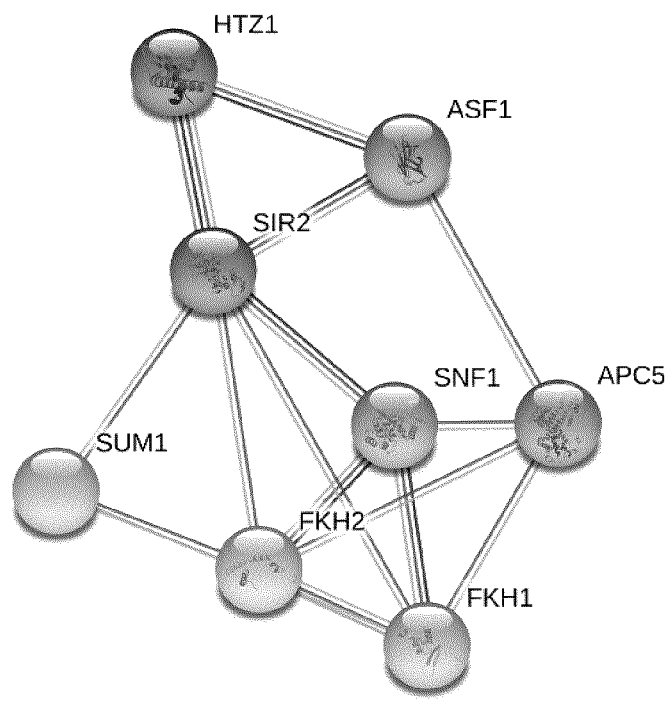

As mentioned above, sequencing of C43-4 and C2-4B revealed that C43-4 shared sequence homology with Htz1, while C2-4B was similar to Sum1 (FIGS. 4, 5). Using a STRING analysis (http://string-db.org), it was observed that Htz1 and Sum1 interacted within a network that included Apc5, as well as Apc5 interacting proteins Fkh1, Fkh2, Asf1 and Snf1, which was centered by the major stress response and longevity protein Sir2 (FIG. 6). Fkh1, Fkh2, Snf1 and Asf1 are also required for response to stress.

Figure 3B:
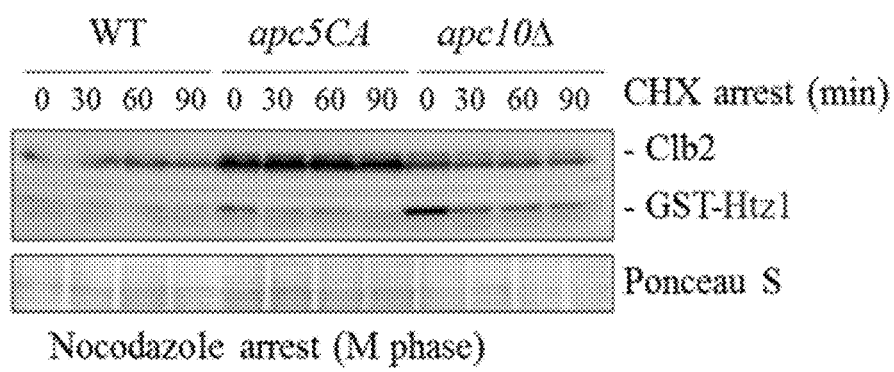

C43-4 is 20 residues long, with a 13 amino acid stretch sharing 46% identity and 85% similarity with a 13 residue region in Htz1, defining a motif of potential significance. Htz1 is a histone H2A variant that responds to DNA damage by recruiting Gcn5, a histone acetyltransferase, to promoters to acetylate histones and increase transcription (Yu et al, 2013). Apc5 and Gcn5 interact to promote H3 acetylation during mitosis (Turner et al, 2010). It is shown here that overexpression of GST-HTZ1 in APC mutants suppressed temperature sensitive (ts) growth and sensitivity to H2O2 (FIG. 3A) and, in WT cells, caused increased Apc10 protein accumulation, while it accumulated and was stabilized in APC mutants (FIGS. 3B and 3C). Previous work showed that increased Apc10 in cells prolonged replicative lifespan (Harkness et al. 2004). Without being bound by theory, this could reflect an interaction between Gcn5 and Htz1 that elevates APC activity by increasing APC subunit levels under stress conditions. In conclusion, the small peptides C43-4 and C2-4B suppressed APC defects, increased stress resistance, and enhanced lifespan.

Using a forward genetic screen to test whether temperature sensitive (ts) APC mutants expressing random small peptides could grow at restrictive temperatures, millions of small peptides were rapidly screened for those that could restore mutant APC phenotypes. Peptides that rescued the apc5$^{CA}$ ts (temperature sensitive) defect were recovered including peptides Y65 and Y36.

One peptide in particular, Y65, was of interest because it had homology to Elongin C (Elc1; Y65 is 20 amino acids in length, with a 7 residue stretch sharing 86% identity and 100% similarity with Elc1). Elc1 is a ubiquitin-protein ligase (E3) conserved among eukaryotes that is involved in DNA repair (Harreman et al, 2009; Ribar et al, 2007). To identify what the peptides bound in order to modify APC activity, Y65 was cloned into the Y2H bait vector and used to identify binding partners. One peptide binding partner was isolated, Cin5, a transcription factor that is induced when stressed.

Figure 7A:
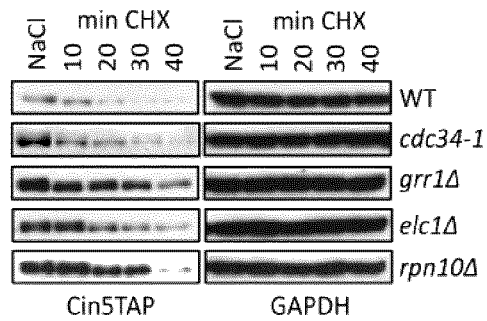
Figure 7B:
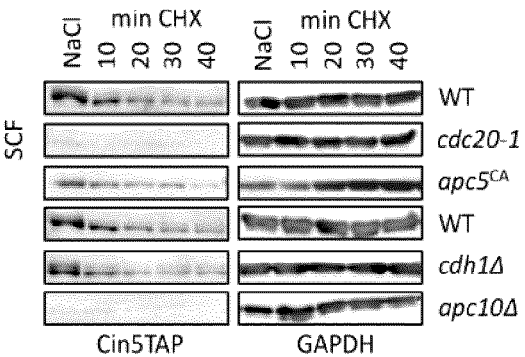

It was observed that Cin5 protein is at low levels and unstable under normal conditions, but accumulated upon a variety of stresses, as observed by others (Nevitt et al, 2004). Cin5 degradation depends on the proteasome, as it is stable in the proteasome mutant rpn10Δ (FIG. 7A). It was found that mutations to the SCF (Skp/Cullin/F-Box) E3, which works in opposition to the APC, stabilized Cin5 (FIG. 7A), whereas mutations that impair APC mitotic function (cdc20-1), but not G1 function (cdh1Δ), cause further Cin5 degradation (FIG. 7B). Thus, without being bound by theory, the ubiquitin pathway (APC and SCF; FIG. 7; APC structure shown in FIG. 8) appears to play a complex role in Cin5 stability, allowing flexible adaptation to stress.

Methodology

Figure 9:
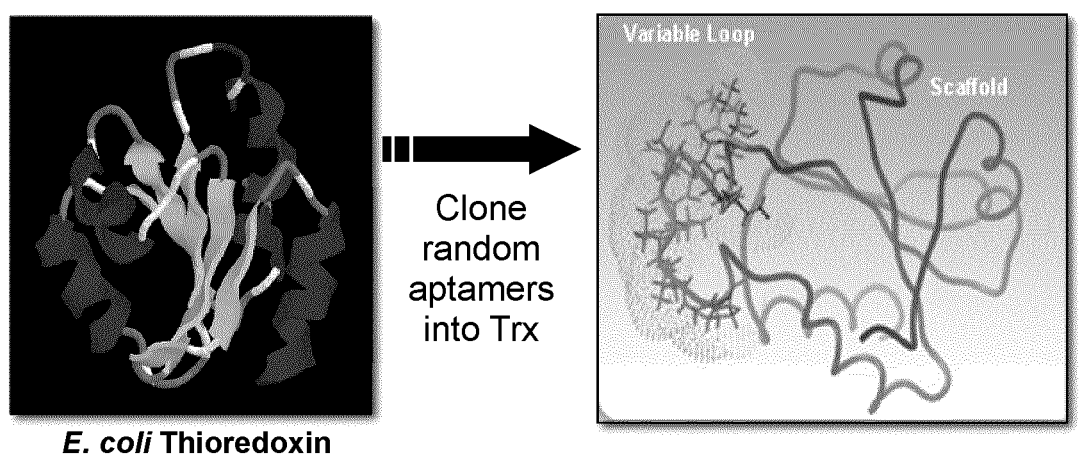

To identify peptides that bound to either Apc5 or Apc10 proteins using a yeast 2-hybrid (Y2H) screen, random small peptides were cloned into the TrxA scaffold (library provided by R. Geyer; FIG. 9) and expressed from a galactose-inducible Y2H prey vector in cells harboring either the APC5 or APC10 genes cloned into the Y2H bait vectors (APC5/APC10 bait constructs complement APC mutant defects).

Over 100 peptides that bound either Apc5 or Apc10 were recovered from millions screened. Six peptides that reproducibly interacted with the Apc5 or Apc10 bait construct in Y2H assays were examined further. Vectors expressing these 6 peptides were transformed into WT or APC mutant cells and assessed for ts growth.

In the forward screens, with galactose-inducible TrxA-based peptide libraries, in cells harboring the apc5$^{CA}$ ts allele, over 200 peptides (from millions screened) suppressed the ts phenotype. Several recovered plasmids were sequenced.

Example 2

As described in Example 1 above, small peptides have been identified that bind the APC and/or suppress APC mutants. These peptides increase longevity and make yeast cells more resistant to stressors. In particular, a small peptide with a protein sequence similar to that of histone protein Htz1 that increased longevity and resistance to stress was identified (C43-4).

Figure 10:
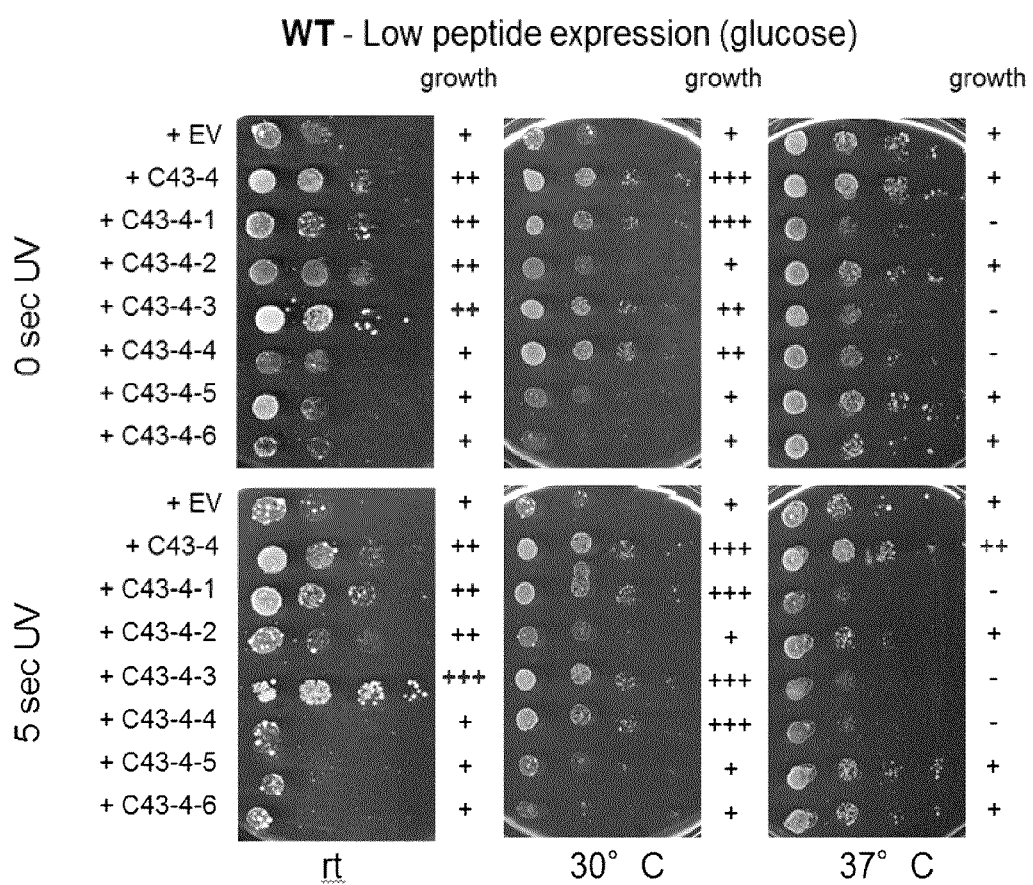

Residues 2, 7, 8, 10, 12 and 14 of peptide C43-4 are conserved with Htz1. All of these residues were mutated to alanine (FIG. 10). Peptides that contained mutations designed to determine which amino acids were required for function were generated. These mutant peptides were grown in wild type cells and in cells that had APC10 mutated, under temperature and UV stress conditions (FIGS. 10-12).

Results

Figure 11:
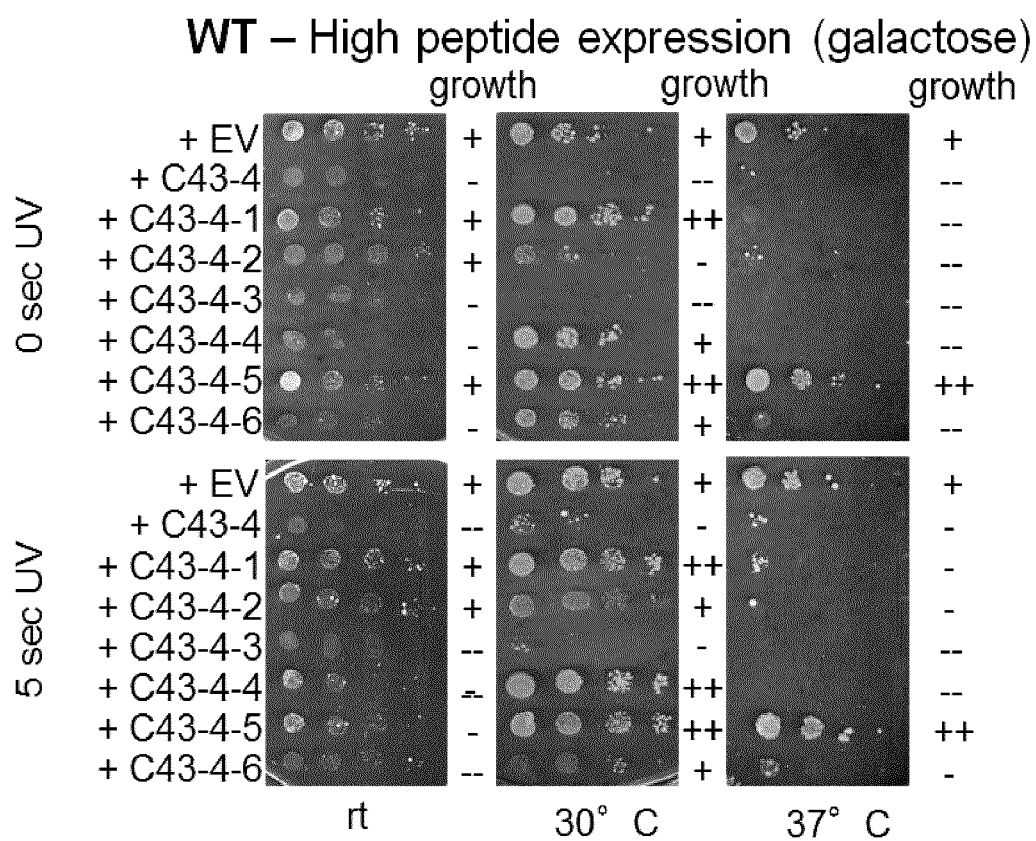
Figure 12:
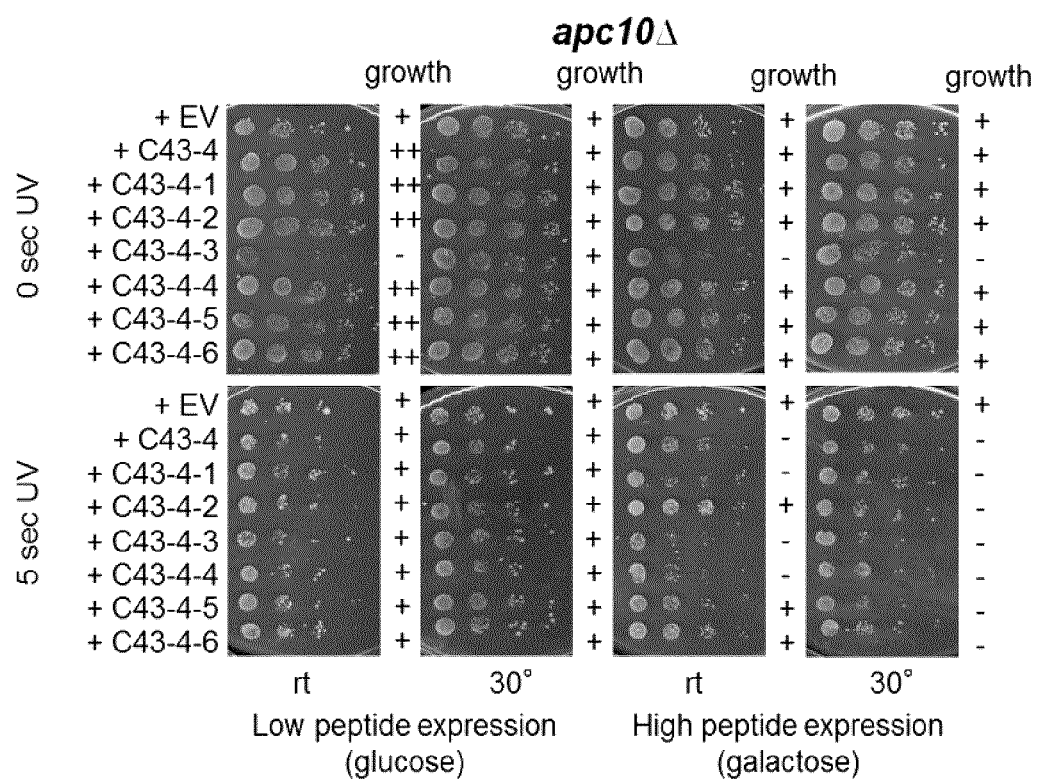
FIG. 12 shows various C43-4 mutant peptides expressed in apc10Δ cells and grown on glucose or galactose media at the temperatures show. The cells were exposed to 5 sec of UV from a UV box prior to incubation.

Galactose inducible C43-4 peptides, that had been mutated at 6 amino acids that are conserved with Htz1, were expressed in wild type (WT) cells. The mutated sequences set out below:

These cells were spot diluted on Trp$^-$ plates and grown at the temperatures shown and/or exposed to ultraviolet (UV) irradiation (FIGS. 10-12). At low level expression on glucose, some of the mutations caused stress dependent phenotypes. The peptide at low levels required at least three different amino acids, as mutants C43-4-2, C43-4-5 and C43-4-6 were similar to the empty vector.

At low level expression (FIG. 10), the WT peptide increased stress resistance. Mutant C43-4-3 increased stress resistance further, likely by increasing the activity of the peptide.

In addition, the peptide required wild-type amino acids at position numbers 7, 12 and 14 for function.

FIG. 11 shows peptides expressed in WT cells and grown on galactose media to induce the peptides at the temperatures shown. The cells were exposed to 5 sec of UV from a UV box prior to incubation. The plus signs define growth compared to the empty vector control.

Expression of the WT and mutant peptides have reduced activity in apc10Δ cells (FIG. 12). Only the C43-4-3 mutant remained toxic in these cells, again consistent with increased activity of this mutant. Since there is reduced activity of these mutants in apc10Δ, this strongly suggests that the peptides do indeed interact with Apc10.

Methods
1. Cells were cultured overnight in Trp$^-$ 2% glucose media
2. The growth of the cells was determined by measuring the optical density (OD) of the cells at 600 nm (OD$_{600}$)
3. Cells were diluted to OD$_{600}$ of 1 with fresh culture media
4. 100 ul of each culture was pipetted into a well of a 96 well plate
5. 10 ul of the each starting culture was pipetted into 90 ul of water in 4 additional wells to make a 10-fold serial spot dilution
6. 5 ul from each serial dilution was spotted onto plates containing standard growth media with either 2% glucose or 2% galactose using a multi-pipettor
7. The plates were exposed to UV
8. The plates were then placed at room temperature, 30, or 37° C. for 3-7 days
9. The plates were scanned and saved as tiff files

| Mutant | Alternative reference | Description | Sequence | SEQ ID NO: |
|---|---|---|---|---|
| C43-4-1 | C43-G2A | alanine at position 2 of C43-4 | NASSHNDLRVRRLTLISRLC | 18 |
| C43-4-2 | C43-D7A | alanine at position 7 of C43-4 | NGSSHNALRVRRLTLISRLC | 19 |
| C43-4-3 | C43-L8A | alanine at position 8 of C43-4 | NGSSHNDARVRRLTLISRLC | 20 |
| C43-4-4 | C43-V10A | alanine at position 10 of C43-4 | NGSSHNDLRARRLTLISRLC | 21 |
| C43-4-5 | C43-R12A | alanine at position 12 of C43-4 | NGSSHNDLRVRALTLISRLC | 22 |
| C43-4-6 | C43-T14A | alanine at position 14 of C43-4 | NGSSHNDLRVRRLALISRLC | 23 |

Example 3

Anaphase Promoting Complex (APC) Substrates Elevated in Canine Lymphoma

Study Set Up

Enrolled companion canines that presented to the Western College of Veterinary Medicine in Saskatoon with lymphoma that had failed CHOP therapy were enrolled in the study. Canine lymphoma is very common, almost always results in a drug resistant form, and is treated identically in humans and canines.

Canines were provided metformin as adjunct therapy as many meta-analyses show that people on metformin have reduced incidence of cancer. It has also been shown that metformin prevents and reverses multiple drug resistant breast cancer in vitro (Davies et al. 2017, PLoS ONE).

Each week tumor tissue was received to use for western determination of MDR markers and RNA microarrays.

Results

Figure 13:
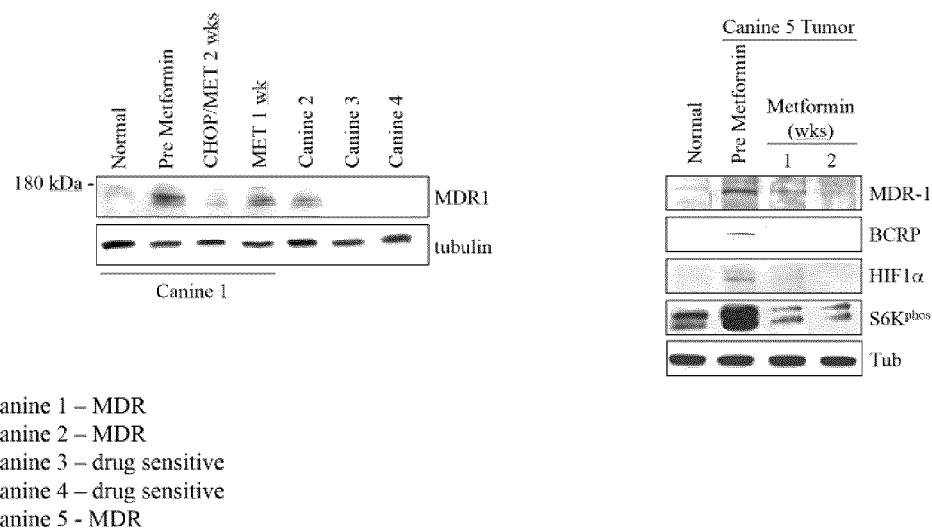
FIG. 13 shows that metformin reverses markers of multiple drug resistance in an in vivo canine model of drug resistant lymphoma.

Metformin was shown to reverse markers of multiple drug resistance in an in vivo canine model of drug resistant lymphoma (FIG. 13).

In addition, microarray analysis on RNA isolated from MDR tumors from 4 canines compared to skin controls showed that they had 293 upregulated genes in common. Using STRING analyses of the 293 gene set, 201 genes were shown to form a highly interconnected network. Many of these genes are involved in cell cycle passage through mitosis and in chromosome maintenance and include many Anaphase Promoting Complex substrates.

Figure 14A:
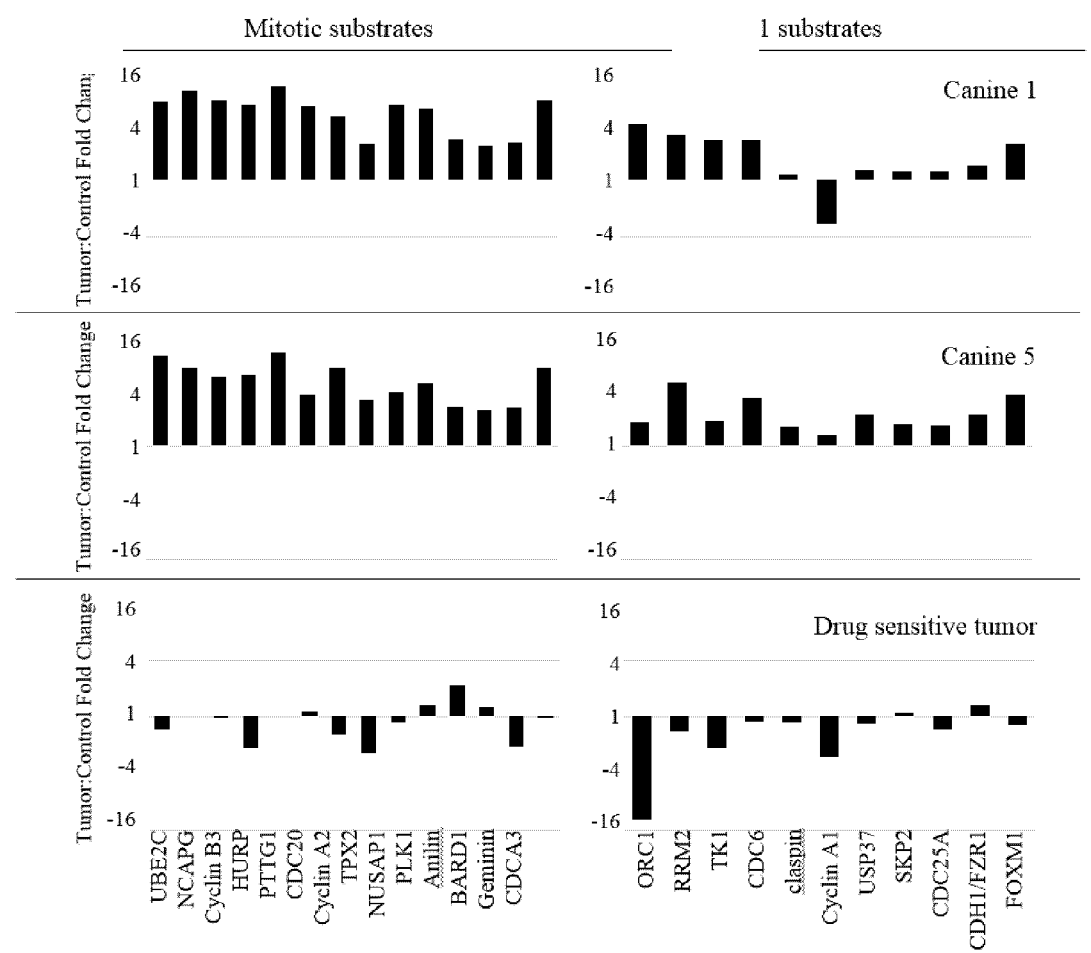
FIGS. 14(A and B) shows that multiple APC mitotic substrate RNAs are elevated in canine tumors. For each pair, the left box is "M Phase APC substrate FC" and the right box is "G1 APC substrate FC".
Figure 14B:
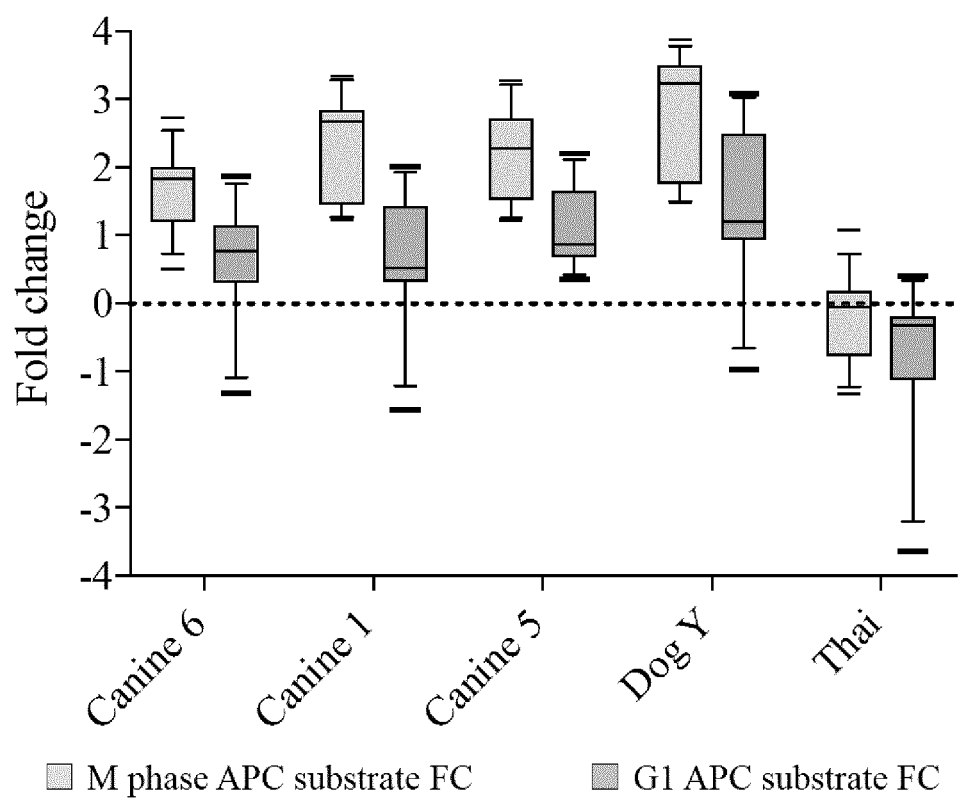

As shown in FIG. 14 (A and B), multiple APC mitotic substrate RNAs are elevated in all 4 canine tumors sampled.

Figure 15:
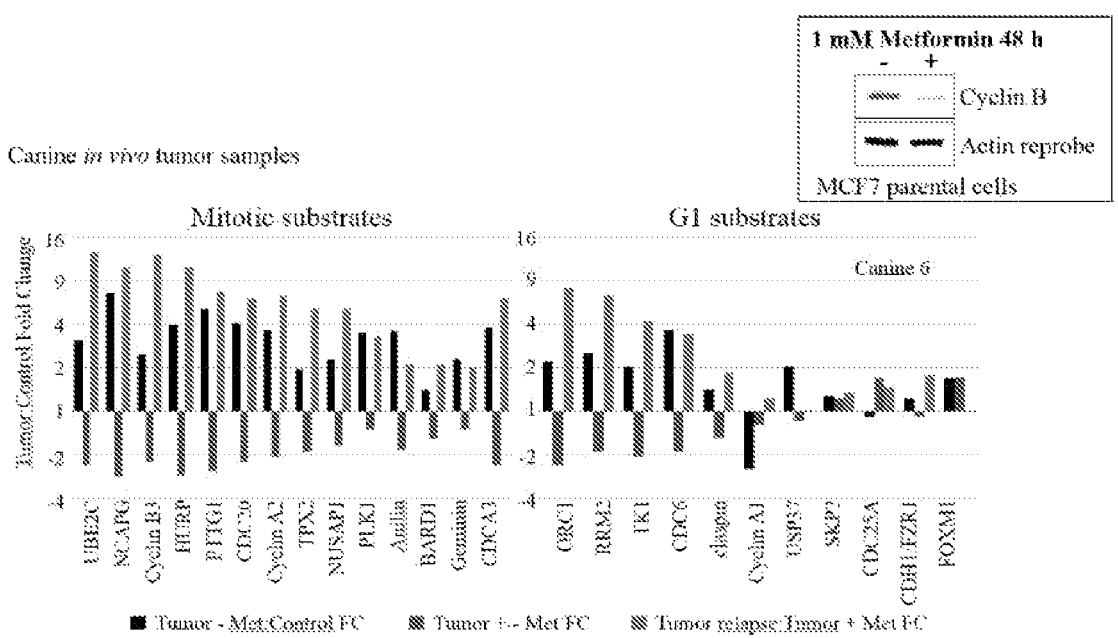
FIG. 15 shows that in one canine, metformin induced remission and reduced APC substrate RNA levels, while relapse resulted in elevated APC substrate levels. For each triplet, the left bar is "Tumor−Met:Control FC", the middle bar is "Tumor+/−Met FC" and the right bar is "Tumor relapse: Tumor+Met FC".

One canine (canine 6) entered remission after failing all other treatment options. RNA was sampled from the MDR tumor, during metformin treatment, during tumor shrinkage and remission and during relapse and microarray analysis was performed. Metformin induced remission and reduced APC substrate RNA levels, while relapse resulted in elevated APC substrate levels (FIG. 15).

Example 4

APC Activity Diminished in Cancer Cells

APC mitotic substrates are elevated in 24 different human patient tumor samples from many different cancer types (FIG. 16).

APC mitotic protein substrates are also elevated in a canine lymphoma cell line selected for Doxorubicin resistance (FIG. 17).

APC mitotic substrates are also elevated in human MCF7 breast cancer cells selected for Tamoxifen resistance (FIG. 18).

Example 5

Activation of the APC Provides a Benefit to Cells

APC activator Mad2 Inhibitor-1 (M2I-1) is a small molecule that binds MAD2. MAD2 acts to inhibit APC function by sequestering away the APC activator CDC20. By disrupting the MAD2/CDC20 interaction, M2I-1 causes the APC to become activated earlier than usual.

Figure 19A:
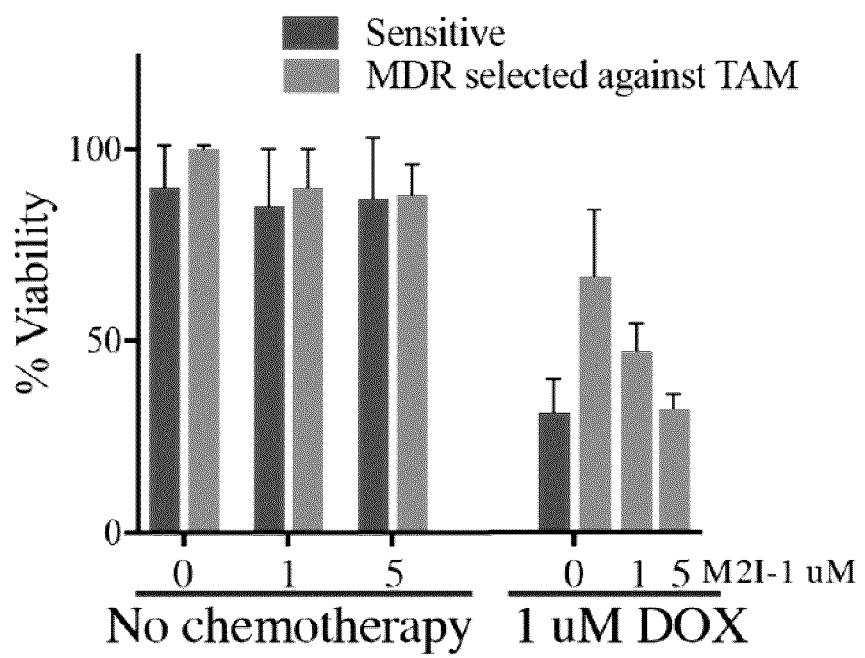
Figure 19B:
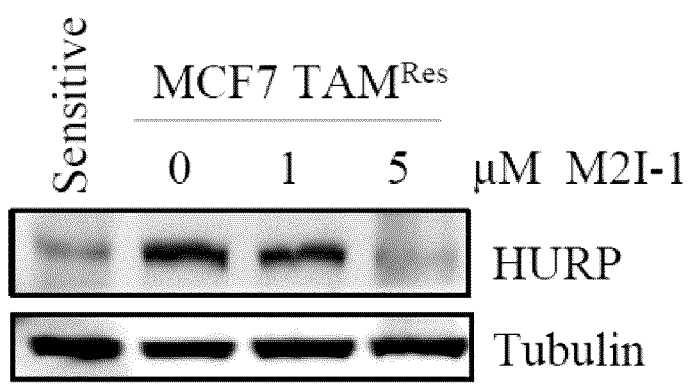
Figure 19C:
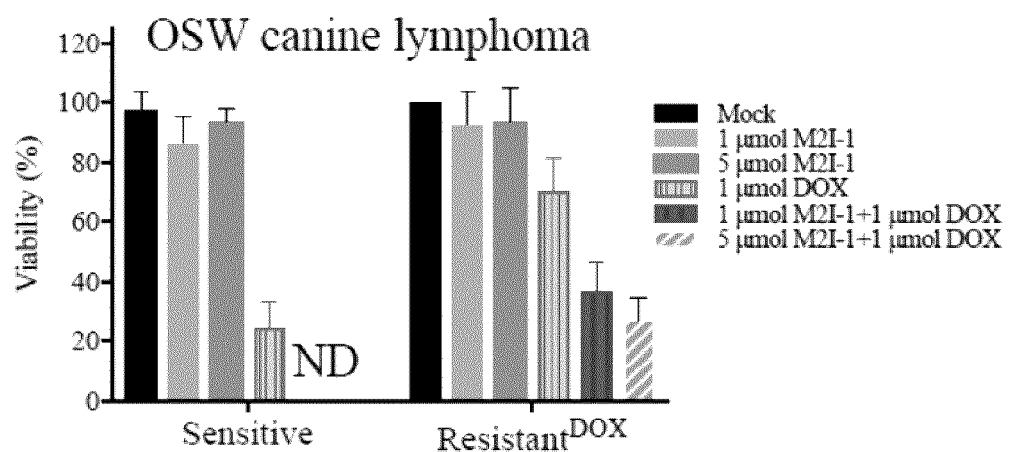
Figure 19D:
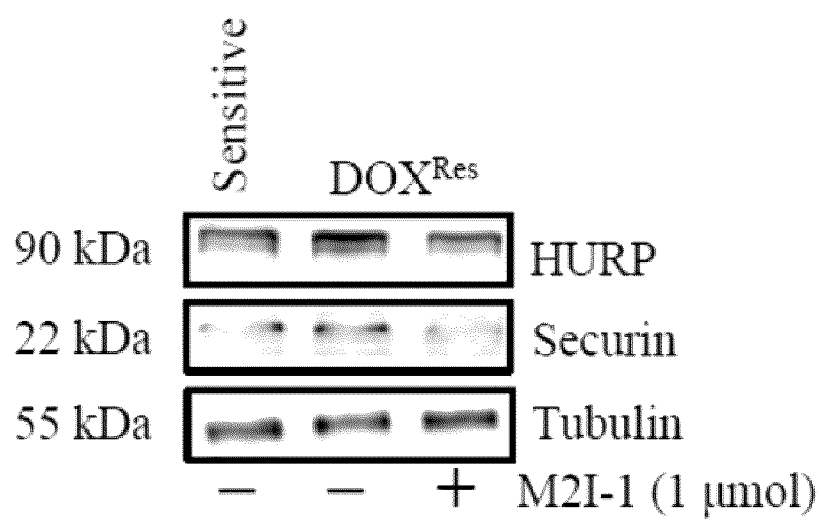
Figure 19E:
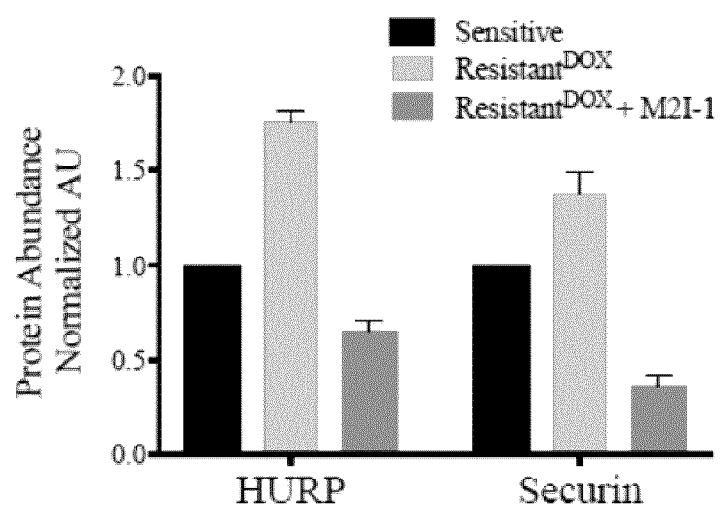

Human MCF7 breast cancer cells selected for resistance to Tamoxifen were treated with the M2I-1 activator in culture. M2I-1 did not impair the growth of these cells alone (FIG. 19A), but reduced the levels of several APC substrates tested (FIG. 19B), showing that the APC was activated. When chemotherapy was used with or without M2I-1, only in the presence of M2I-1 were cells killed (FIG. 19A). This was observed in chemotherapeutic resistant cells generated from both human MCF7 breast cancer cells (FIGS. 19A and 19B) and in OSW dog lymphoma cells (FIGS. 19C-E) selected for chemotherapeutic resistance. Without being bound by theory, these results suggest that activating the APC may be a general mechanism of protecting against chemotherapeutic resistance and are not cell line or species specific.

A mouse model for growing patient derived breast tumor cells obtained from a patient with triple negative breast cancer was developed. This patient had developed resistance to Doxorubicin. Tumors growing in these mice grow rapidly. Mice growing the patient derived xenografted (PDX) tumor were injected with various amounts of M2I-1. It was observed that tumor growth was stalled in these cells in a dose-dependent manner, and markers of APC substrates were positive for APC activation in the tumor (FIGS. 20A, 20B). Since the APC was activated in the canines tested in this study following treatment with metformin, it was asked if metformin can directly activate the APC. Reduced APC substrate Cyclin B levels following metformin treatment in human MCF7 breast cancer cells was observed, similar to that observed when MDF7 cells express the C43-4 plasmid (see below for more on this plasmid) (FIG. 21).

Without being bound by theory, reduced APC activity may be associated with aggressive cancers, while increased APC activity appears to sensitize cancer cells, both in vitro and in vivo, to chemotherapy.

Example 6

C43-4 Peptide Sensitizes Cells to Chemotherapeutics

Figure 22A:
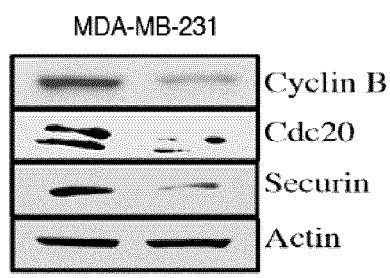
Figure 22B:
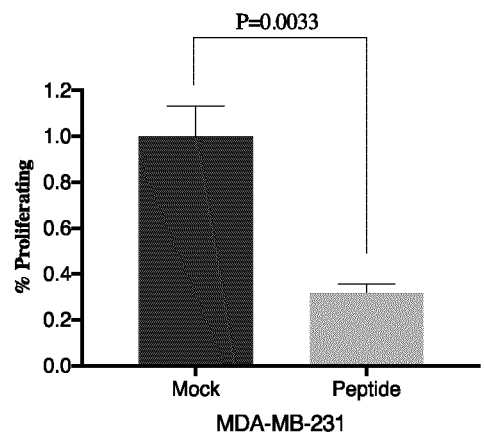
Figure 23A:
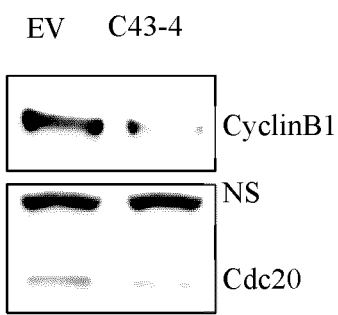
Figure 23B:
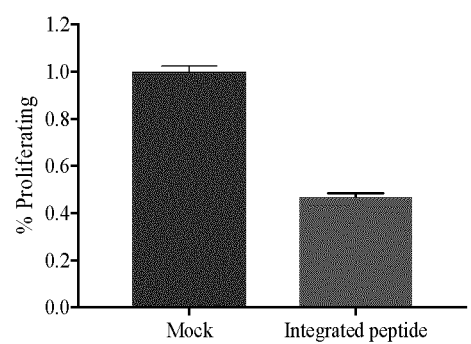
Figure 24A:
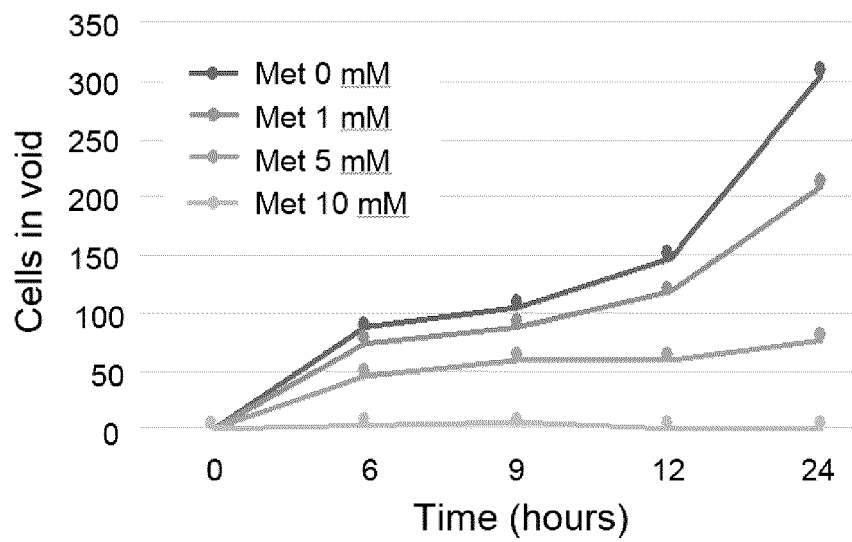
Figure 24B:
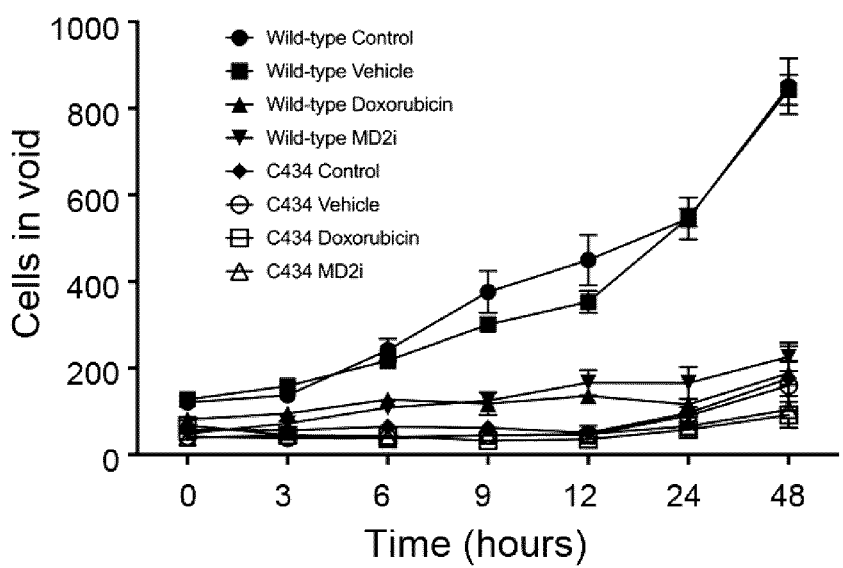
Figure 24C:
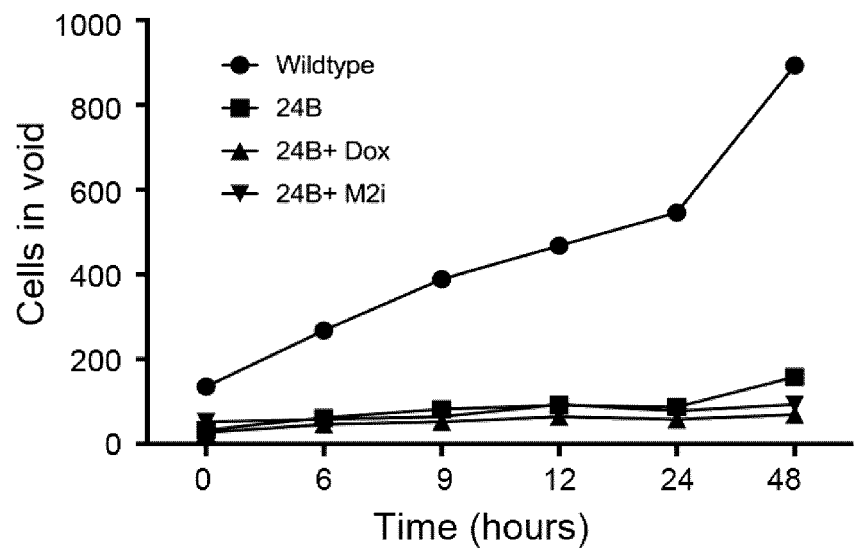
Figure 24D:
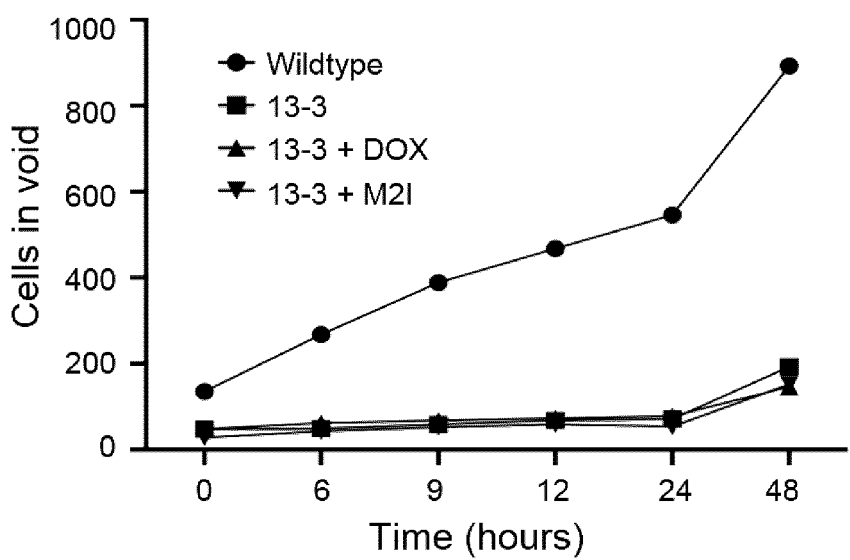

The C43-4 peptide sequence was cloned into the human expression vector pcDNA. This construct was transiently, and stably, expressed in human breast cancer cell line MDA-MB-231. In transiently transfected cells, the APC substrates Cyclin B, Cdc20 and Securin were reduced, indicating that C43-4 activated the APC (FIG. 22A). In stably transfected MDA-MB-231 cells, C43-4 reduced protein levels of CyclinB (FIG. 23A). In 231 cells, which are triple negative, aggressive and somewhat resistant to Doxorubicin, the transiently and stably transfected C43-4 peptide resensitized them to DOX treatment (FIGS. 22B and 23B).

Example 7

Metastatic Potential of MDA-MB-231 Cells is Blocked by Metformin, Doxorubicin, the APC Activator Compounds M2I-1 and TTKi, and by the APC Activating Peptides C43-4, C2-4B and C13-3.

As shown in FIGS. 24A-D, the metastatic potential of MDA-MB-231 cells is blocked by the anticancer drugs metformin (FIG. 24A) and Doxorubicin, and by activation of the APC (FIGS. 24B-D); both the chemical APC activators M2I-1 and TTKi, and the APC activating peptides C43-4, C2-4B and C13-3 inhibit the in vitro migration of MDA-MB-231 cells using a scratch assay. Assays using WT and C43-4 expressing cells have been done 4 times. Assays using C13-3 and C2-4B cells have only been conducted once. Metformin treated cells have been used twice. For scratch assays, a scratch is made down a confluent plate of cells, leaving a void. The number of cells that migrate back into the void over time is determined.

Example 8

Figure 25A:
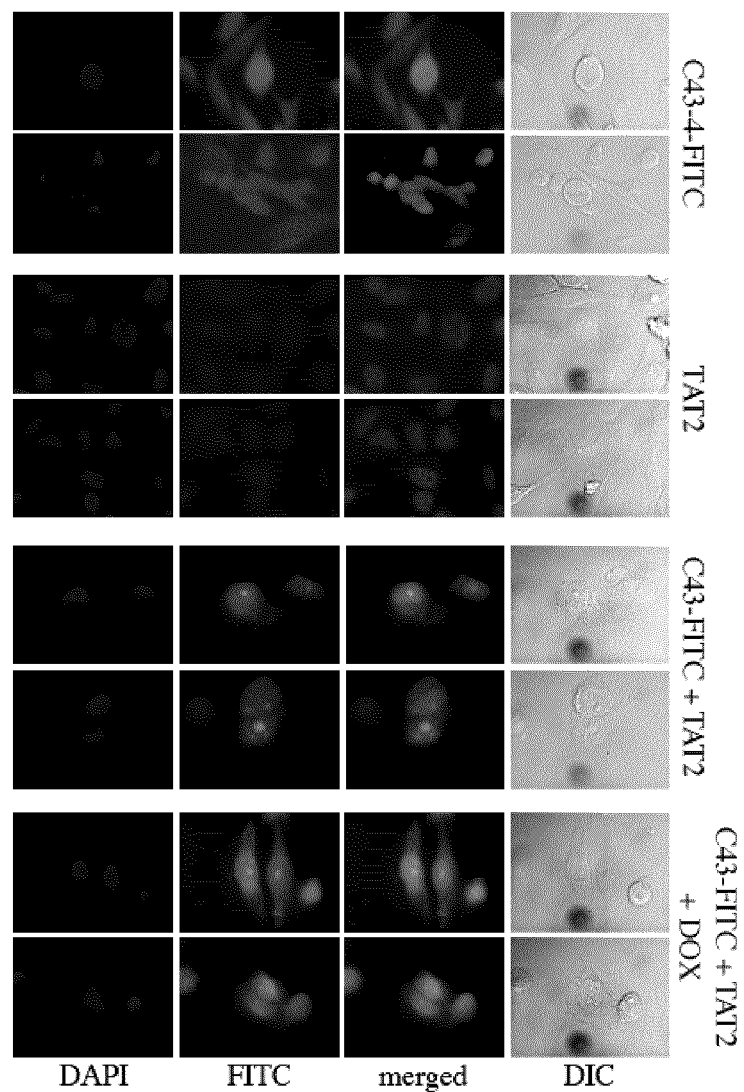
Figure 25B:
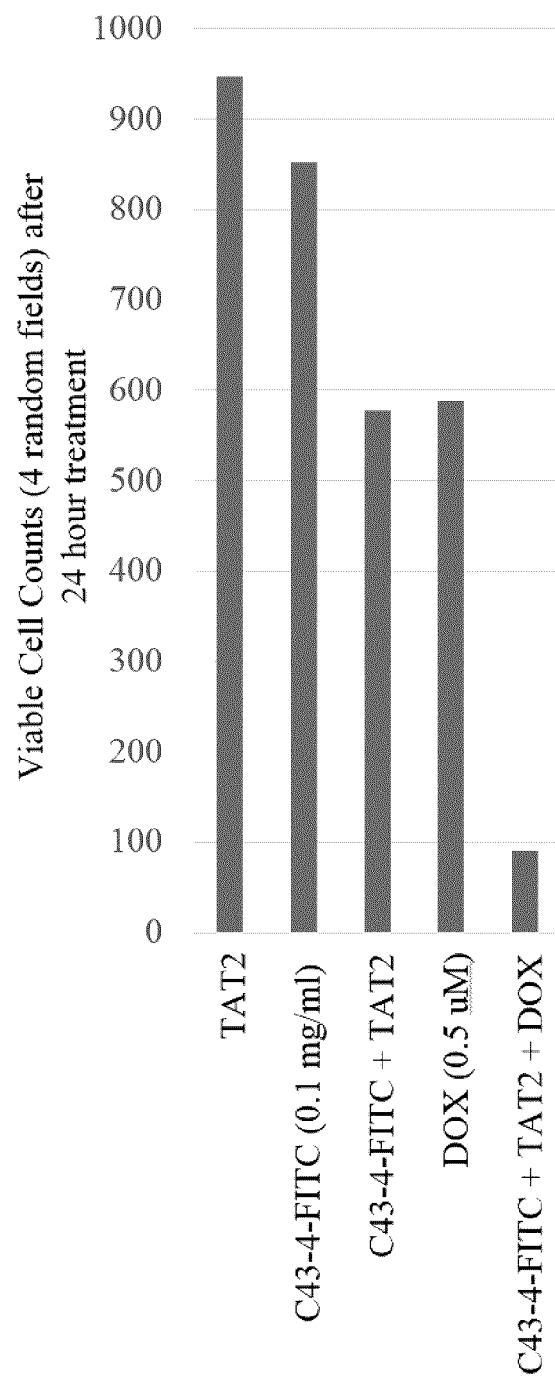
Figure 25C:
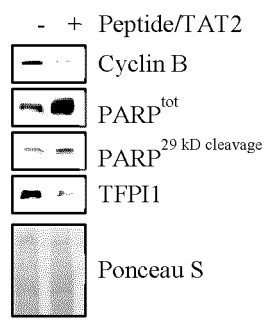
Figure 25D:
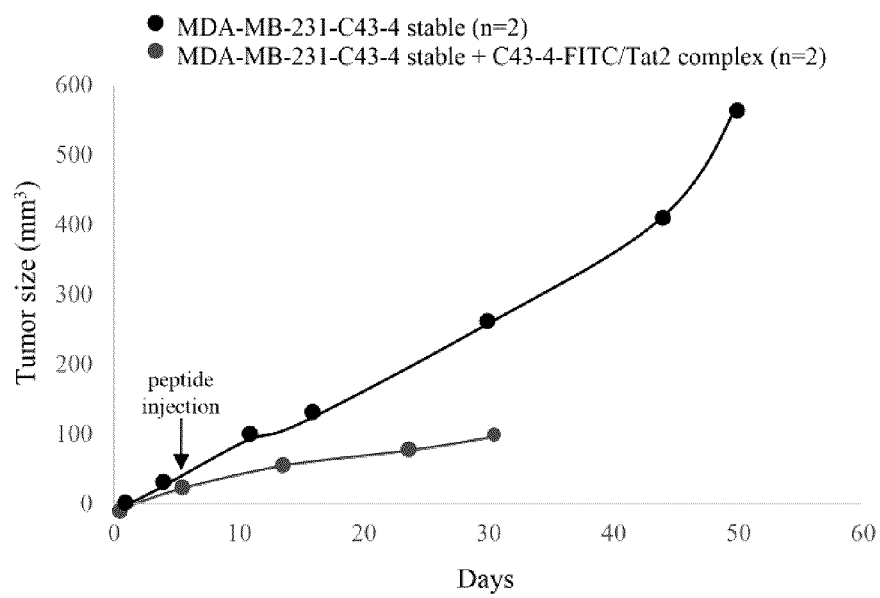

The 20 amino acid C43-4 peptide was synthesized with a C-terminal FITC epitope to allow visualization of the peptide within the cell using fluorescent microscopy. The TAT2 cell penetrating peptide, encoding 2 copies of a 9 amino acid peptide (RKKRRQRRRRKKRRQRRR; SEQ ID NO: 26) was also synthesized. TAT2 and C43-4-FITC form a complex that allows transport of C43-4-FITC across membranes and into cells. The C43-4-FITC/TAT2 complex was then added to cell culture growth media, showing that the complex can enter triple negative breast cancer MDA-MB-231 cells and localizes within nuclei (FIG. 25A—the bright spots within the nuclei in C and D are nucleoli showing that the C43-4-FITC/TAT2 complex enters the nucleoli). Cell toxicity was only observed when C43-4-FITC was complex with TAT2, and toxicity was worsened with DOX (FIG. 25B). For this experiment, cells imaged in FIG. 25A were grown and treated on cover slips. An equal number of cells were added to cover slips and treated in the manner described in FIG. 25B. After 24 hours, and prior to imaging, 4 independent microscope fields were counted for each sample and added together to get a total cell number. MDA-MB-231 cells treated with the complex show early signs of apoptosis (increased 29 kD PARP cleavage fragment) and reversal of a multiple drug resistance (reduced TFPI, a marker of multiple drug resistance) (FIG. 25C).

A single IP injection of the C43-4-FITC/TAT2 complex into mice growing triple negative breast cancer MDA-MB-231 cells stably expressing the C43-4 plasmid slows tumor growth for at least 10 days without adverse side effects (FIG. 25D). 100 ul of 0.01 mg/ml C43-4-FITC peptide was mixed with 25 ul of 1 mg/ml TAT2. The entire 125 ul was given to the mouse using an intraperitoneal (IP) injection. Only the 1 injection given in this experiment was sufficient to inhibit tumor growth over the time frame of the experiment.

Example 9

Testing of Additional Peptides

Figure 26A:
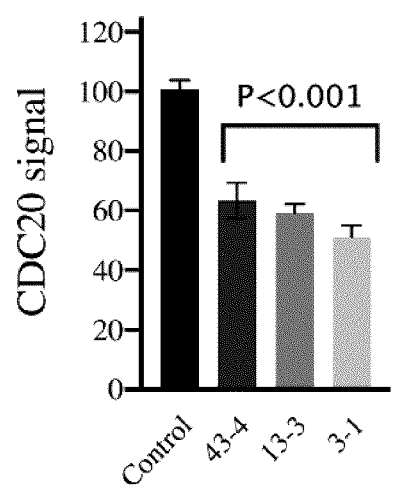
Figure 26B:
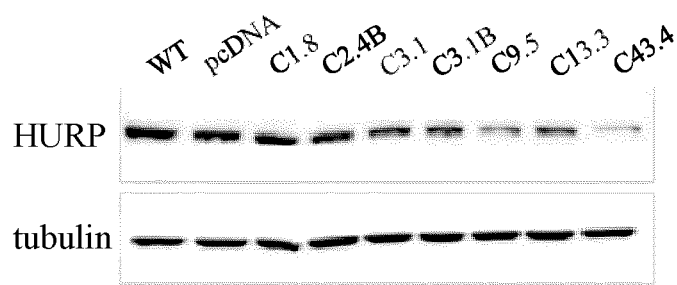
Figure 26C:
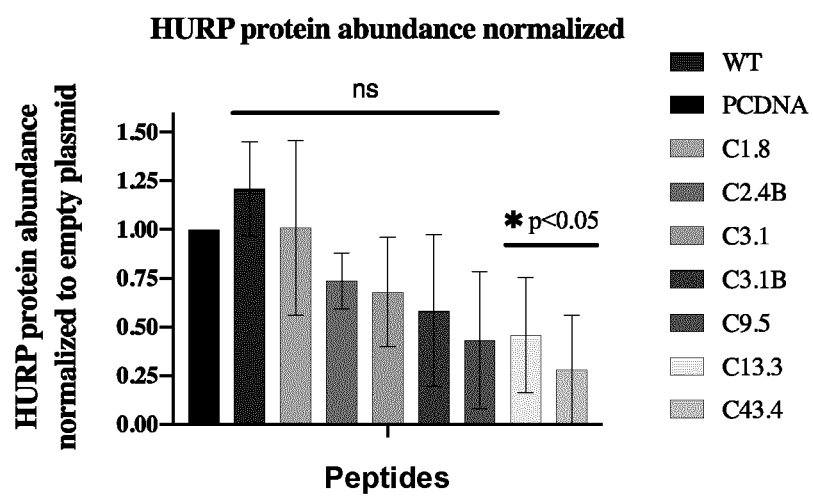
Figure 26D:
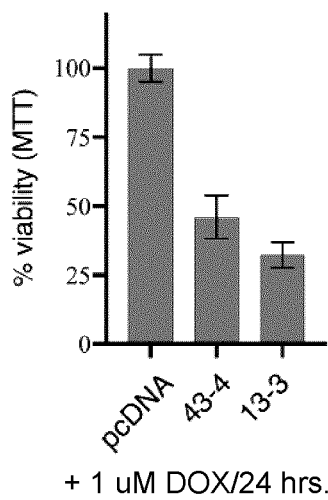

In FIG. 26A, it is shown that C13-3 and C3-1 reduce levels of the APC substrate CDC20, similar to C43-4, indicating that these peptides can all activate the APC in triple negative breast cancer MDA-MB-231 cells. In FIG. 26B, MDA-MB-231 cells were also stably transfected with the peptides C1-8, C2-4B, C3-1B, and C9-5. Levels of the APC substrate HURP were measured in lysates prepared from these cells. Tubulin shows that equal protein was assessed in each lysate. The levels of HURP were quantitated, normalized to tubulin and shown in FIG. 26C. Only C1-8 did not reduce HURP levels. The empty vector pcDNA was also stably expressed in 231 cells and used as a control. To show that activation of the APC is relevant in these cancer cells, stably transfected pcDNA, C43-4 and C13-3 cells were treated with 1 uM Doxorubicin for 24 hours. The results show that the peptides synergize with the anti-cancer drug Doxorubicin, increasing the killing effect of Doxorubicin (FIG. 26D).

HA Tagged C43-4 Peptide

HA tagged C43-4 peptide fused to the thioredoxin backbone can be detected using antibodies against HA (FIG. 27). As a control, Cyclin B1 levels were also measured and actin was used as a load control. Mock treated cells were also included as a control to show the specificity of the HA band. The HA band migrates at the expected 34 kD.

TABLE 1

The peptides listed below (a) increase the viability of an apc5$^{temperature}$ sensitive mutant and/or an apc10Δ mutant and (b) bind the APC.

| Peptide sequence | | SEQ ID NO: | Notes |
|---|---|---|---|
| NGSSHNDLRVRRLTLISRLC | C43-4 | 1 | Binds Apc10<br>Residues 2-14<br>(GSSHNDLRVRRLT;<br>SEQ ID NO: 12) overlap<br>with Hzt1 in yeast.<br>Various degrees of<br>similarity to Htz1, Cst9,<br>Rpt1 (proteasome), Svf1<br>(survival pathway), Elm1<br>(Snf1 kinase) and Ddc1<br>were determined using a<br>BLAST search. |
| NGSSHNDARVRRLTLISRLC | C43-4-3;<br>C43-<br>L8A | 2 | Version of C43-4 where<br>the leucine residue at<br>position 8 is replaced<br>with alanine<br>The following motif was<br>identified in several<br>different peptide<br>sequences: SSH |
| CECLETETFHPITRHLIVPV | C9-5 | 3 | Residues 5-19<br>(ETETFHPITRHLIVP;<br>SEQ ID NO: 13) overlap<br>with Swe1 in yeast/Wee1<br>in humans<br>Binds Apc5<br>Shares similarity with<br>Die2, Tim44, Yrm1 and<br>Scp160; identified using<br>a BLAST search |

TABLE 1-continued

The peptides listed below (a) increase the viability of an apc5$^{temperature}$ sensitive mutant and/or an apc10Δ mutant and (b) bind the APC.

| Peptide sequence | | SEQ ID NO: | Notes |
|---|---|---|---|
| RMPQWWQWMWV | C2-4B; 11-3 | 4 | Has homology with yeast protein Sum 1. Residues 1-9 (RMPQWWQWM; SEQ ID NO: 14) overlap with Naf1 in yeast/NAF1 in humans. Naf1/NAF1 is involved in pre-rRNA processing<br>Binds Apc10<br>Shares similarity with Sum1, Vas1, Shh3, Dbr1; identified using a BLAST search |
| PSYNTIKYHETHGGRHPRRQRKRPI | C3-1 | 5 | Binds Apc10 |
| GALKEVCICIVESVGGEVFS | 4; also referred to as C13-3 | 6 | Binds Apc5<br>Shares homology with Hxt2, Mad2, Ubc7, Rpp2, Kap122, Sfa1, Oac1 and Vps13 identified using a BLAST search |
| SKWTWRMCMSWTVDRFAPVPWP | C24-1 | 7 | Binds Apc5<br>Shares similarity with Nup82, Sc53, Syf1 and Kap104; Identified using BLAST<br>The following motifs were identified in several different peptide sequences: SKWT and MCMS |
| FCL | C1-8 | 8 | |
| RRCLSIRTENLAWEGKFLRV | C50-1 | 9 | Binds Apc10<br>Shares similarity with Pxa1, Rrp12, and Hfm1; Identified using BLAST |
| PVNGERWAP | C3-1B | 15 | Binds Apc10 |
| GRMLMTYLMYFMVLWVPRPWGPPL | | 16 | |

TABLE 2

The peptides listed below increase the viability of an apc5$^{temperature}$ sensitive mutant

| Peptide sequence | | SEQ ID NO: | Notes |
|---|---|---|---|
| VRQKSDKEYERVLGLGLRRL | Y65 | 10 | Rescues apc5$^{CA}$ temperature sensitive (ts) growth but does not bind the APC in a yeast 2HY assay<br>Has homology with yeast protein Elc1 as well as Spc110 (cohesion complex), Cbs2, Stb2 and Tfb3<br>Interacts with Cin5 in a yeast 2 hybrid assay |

TABLE 2-continued

The peptides listed below increase the viability of an apc5$^{temperature}$ sensitive mutant

| Peptide sequence | SEQ ID NO: | Notes |
|---|---|---|
| SWLNGSGGVVLWLFSNFCCG Y36 | 11 | Rescues apc5$^{CA}$ temperature sensitive (ts) growth but does not bind the APC in a yeast 2HY assay |

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety.

REFERENCES

Harkness T A, Shea K A, Legrand C, Brahmania M, Davies G F. (2004). A functional analysis reveals dependence on the anaphase-promoting complex for prolonged life span in yeast. Genetics 168:759-74.

Postnikoff S D, Harkness T A. (2014). Replicative and chronological life-span assays. Methods Mol Biol 1163: 223-7.

Postnikoff S D, Malo M E, Wong B, Harkness T A. (2012). The yeast forkhead transcription factors fkh1 and fkh2 regulate lifespan and stress response together with the anaphase-promoting complex. PLoS Genet 8:e1002583.

Menzel J, Malo M E, Chan C, Prusinkiewicz M, Arnason T G, Harkness T A. (2014). The anaphase promoting complex regulates yeast lifespan and rDNA stability by targeting Fob1 for degradation. Genetics 196:693-709.

Harkness T A, Davies G F, Ramaswamy V, Arnason T G. (2002). The ubiquitin-dependent targeting pathway in Saccharomyces cerevisiae plays a critical role in multiple chromatin assembly regulatory steps. Genetics 162:615-32.

Harkness T A, Arnason T G, Legrand C, Pisclevich M G, Davies G F, Turner E L. (2005). Contribution of CAF-I to anaphase-promoting-complex-mediated mitotic chromatin assembly in Saccharomyces cerevisiae. Eukaryot Cell 4:673-84.

Turner E L, Malo M E, Pisclevich M G, Dash M D, Davies G F, et al. (2010). The Saccharomyces cerevisiae anaphase-promoting complex interacts with multiple histone-modifying enzymes to regulate cell cycle progression. Eukaryot Cell 9:1418-31.

Islam A, Turner E L, Menzel J, Malo M E, Harkness T A. (2011). Antagonistic Gcn5-Hda1 interactions revealed by mutations to the Anaphase Promoting Complex in yeast. Cell Div 6:13.

Jiao R, Postnikoff S, Harkness T A, Arnason T G. (2015). The SNF1 Kinase Ubiquitin-associated Domain Restrains Its Activation, Activity, and the Yeast Life Span. J Biol Chem 290:15393-404.

Malo M E, Postnikoff S D, Arnason T G, Harkness T A. (2016). Mitotic degradation of yeast Fkh1 by the Anaphase Promoting Complex is required for normal longevity, genomic stability and stress resistance. Aging 8:810-30.

Feser J, Truong D, Das C, Carson J J, Kieft J, et al. (2010). Elevated histone expression promotes life span extension. Mol Cell 39:724-35.

Yu Y, Deng Y, Reed S H, Millar C B, Waters R. (2013). Histone variant Htz1 promotes histone H3 acetylation to enhance nucleotide excision repair in Htz1 nucleosomes. Nucleic Acids Res 41:9006-19.

Millar C B, Xu F, Zhang K, Grunstein M. (2006). Acetylation of H2AZ Lys 14 is associated with genome-wide gene activity in yeast. Genes Dev 20:711-22.

Harreman M, Taschner M, Sigurdsson S, Anindya R, Reid J, et aL (2009). Distinct ubiquitin ligases act sequentially for RNA polymerase II polyubiquitylation. PNAS 106: 20705-10.

Ribar B, Prakash L, Prakash S. (2007). ELA1 and CUL3 are required along with ELC1 for RNA polymerase II polyubiquitylation and degradation in DNA-damaged yeast cells. MCB 27:3211-6.

Hanlon S E, Rizzo J M, Tatomer D C, Lieb J D, Buck M J. (2011). The stress response factors Yap6, Cin5, Phd1, and Skn7 direct targeting of the conserved co-repressor Tup1-Ssn6 in S. cerevisiae. PLoS One 6:e19060.

Furuchi T, Ishikawa H, Miura N, Ishizuka M, Kajiya K, et al. (2001). Two nuclear proteins, Cin5 and Ydr259c, confer resistance to cisplatin in Saccharomyces cerevisiae. Mol Pharmacol 59(3):470-4.

Jackson T, Kwon E, Chachulska A M, Hyman L E. (2000). Novel roles for elongin C in yeast. Biochim Biophys Acta 1491:161-76.

Nevitt T, Pereira J, Rodrigues-Pousada C. (2004). YAP4 gene expression is induced in response to several forms of stress in Saccharomyces cerevisiae. Yeast 21:1365-74.

Thornton B R, Ng T M, Matyskiela M E, Carroll C W, Morgan D O, Toczyski D P (2006) An architectural map of the anaphase-promoting complex. Genes Dev 20: 449-460.

Edwards, A. B., Anderton, R. S., Knuckey, N. W., & Meloni, B. P. (2018). Perinatal Hypoxic-Ischemic Encephalopathy and Neuroprotective Peptide Therapies: A Case for Cationic Arginine-Rich Peptides (CARPs). Brain Sciences, 8(8), 147.

Henriques S T, Costa J, Castanho M A (2005) Translocation of beta-galactosidase mediated by cell-penetrating peptide pep-1 into lipid vesicles and human HeLa cells is driven by membrane electrostatic potential. Biochemistry 44:10189-10198.

Mae M, Myrberg H, Jiang Y, Paves H, Valkna A, Langel U (2005) Internalisation of cell-penetrating peptides into tobacco protoplasts. Biochim Biophys Acta 1669:101-107.

Meloni B. P., Brookes L. M., Clark V. W., Cross J. L., Edwards A. B., Anderton R. S., Hopkins R. M., Hoffmann K., Knuckey N. W. (2015) Poly-arginine and arginine-rich peptides are neuroprotective in stroke models. J. Cereb. Blood Flow Metab. 2015; 35:993-1004.

Pooga M, Kut C, Kihlmark M, Hallbrink M, Fernaeus S, Raid R, Land T, Hällberg E, Bartfai T, Langel Ü (2001) Cellular translocation of proteins by transportan. FASEB J 15:1451-1453.

Rudolph C, Planks C, Lausier J, Schillinger U, Muller R H, Rosenecker J (2003) Oligomers of the arginine-rich motif of the HIV-1TAT protein are capable of transferring plasmid DNA into cells. J Biol Chem 278(13):11411-11418.

Copolovic et al. (2014), Cell-Penetrating Peptides: Design, Synthesis, and APplicatins, ACS Nano, 2014, 8(3) 1972-1994.

The invention claimed is:

1. A method of treating breast cancer, lymphocytic cancer or leukemia in a subject in need thereof, inhibiting the growth of a breast, lymphocytic or leukemia cancer cell and/or reducing resistance to a breast, lymphocytic or leukemia cancer treatment in a cancer cell or subject in need thereof, the method comprising administering a peptide to the subject or cell, the peptide comprising:
the amino acid sequence GSSHNDLRVRRLT (SEQ ID NO: 12).

2. The method of claim 1, wherein the peptide has a maximum length of 30 amino acids.

3. The method of claim 1, wherein the peptide consists of amino acid sequence GSSHNDLRVRRLT (SEQ ID NO: 12).

4. The method of claim 1, wherein the peptide is conjugated to a cell-penetrating peptide.

5. The method of claim 1, wherein the subject is a mammal.

6. The method of claim 1, wherein the cancer is triple negative breast cancer.

7. The method of claim 1, wherein the cancer treatment is a chemotherapeutic.

8. The method of claim 1, wherein the method further comprises administering a chemotherapeutic to the subject.

9. A method of treating breast cancer, lymphocytic cancer or leukemia in a subject in need thereof, inhibiting the growth of a breast, lymphocytic or leukemia cancer cell and/or reducing resistance to a breast, lymphocytic or leukemia cancer treatment in a cancer cell or subject in need thereof, the method comprising administering a composition comprising a peptide and a carrier to the subject or cell, the peptide comprising
the amino acid sequence GSSHNDLRVRRLT (SEQ ID NO: 12).

10. The method of claim 4, wherein the cell-penetrating peptide comprises TAT2, TAT, Pep1, R9, TAT-NBD, Transportan, pVEC, penetratin, VP22, a polyarginine-based peptide or a calcitonin peptide.

11. The method of claim 5, wherein the subject is a human.

12. The method of claim 7, wherein the chemotherapeutic is doxorubicin, rapamycin, capecitabine, carboplatin, cyclophosphamide, gemcitabine, paclitaxel, vinorelbine or tamoxifen.

13. The method of claim 8, wherein the chemotherapeutic is administered prior to, overlapping with, concurrently with, and/or after administration of the peptide.

* * * * *